United States Patent
Lee et al.

(10) Patent No.: US 10,276,804 B2
(45) Date of Patent: Apr. 30, 2019

(54) COMPOUND FOR ORGANIC OPTOELECTRONIC ELEMENT, ORGANIC OPTOELECTRONIC ELEMENT COMPRISING SAME, AND DISPLAY DEVICE

(71) Applicant: SAMSUNG SDI CO., LTD., Yongin-si, Gyeonggi-do (KR)

(72) Inventors: Seung-Jae Lee, Suwon-si (KR); Dong-Min Kang, Suwon-si (KR); Eun-Sun Yu, Suwon-si (KR); Sang-Shin Lee, Suwon-si (KR); Sung-Hyun Jung, Suwon-si (KR); Ho-Kuk Jung, Suwon-si (KR); Su-Jin Han, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 0 days.

(21) Appl. No.: 15/516,757

(22) PCT Filed: Aug. 6, 2015

(86) PCT No.: PCT/KR2015/008245
§ 371 (c)(1),
(2) Date: Apr. 4, 2017

(87) PCT Pub. No.: WO2016/072593
PCT Pub. Date: May 12, 2016

(65) Prior Publication Data
US 2017/0294592 A1    Oct. 12, 2017

(30) Foreign Application Priority Data

Nov. 4, 2014   (KR) .................. 10-2014-0152157

(51) Int. Cl.
| C07D 209/82 | (2006.01) |
| C09K 11/06 | (2006.01) |
| H05B 33/20 | (2006.01) |
| H01L 51/50 | (2006.01) |
| H01L 51/00 | (2006.01) |
| C07D 403/10 | (2006.01) |
| C09K 11/02 | (2006.01) |
| C07D 209/86 | (2006.01) |

(52) U.S. Cl.
CPC ........ *H01L 51/0072* (2013.01); *C07D 209/86* (2013.01); *C07D 403/10* (2013.01); *C09K 11/02* (2013.01); *C09K 11/06* (2013.01); *H01L 51/0067* (2013.01); *H01L 51/50* (2013.01); *H05B 33/20* (2013.01); *C09K 2211/1018* (2013.01); *H01L 51/006* (2013.01); *H01L 51/0061* (2013.01); *H01L 51/0085* (2013.01); *H01L 51/5012* (2013.01); *H01L 51/5016* (2013.01); *H01L 2251/308* (2013.01); *H01L 2251/552* (2013.01); *Y02E 10/549* (2013.01)

(58) Field of Classification Search
CPC ...... C07D 209/82; C09K 11/06; H05B 33/14; H01L 51/5032; H01L 51/5064; H01L 51/5296; H01L 51/0032
USPC ............ 548/440; 257/40, E51.019; 313/501; 428/917
See application file for complete search history.

(56) References Cited

U.S. PATENT DOCUMENTS 9,673,401 B2 *   6/2017   Boudreault ......... H01L 51/0067

FOREIGN PATENT DOCUMENTS

| CN | 101126020 A | 2/2008 |
| CN | 102372696 A | 3/2012 |
| CN | 102884156 A | 1/2013 |
| EP | 2 818 468 A2 | 12/2014 |
| JP | 2005-093159 A | 4/2005 |
| JP | 2005-268199 A | 9/2005 |
| JP | 4843897 B2 | 12/2011 |
| JP | 2012-049518 A | 3/2012 |
| JP | 2012-054227 A | 3/2012 |
| JP | 2014-101275 A | 6/2014 |
| JP | 2014-105208 A | 6/2014 |
| KR | 10-2011-0043342 A | 4/2011 |
| KR | 10-2013-0094222 A | 8/2013 |
| WO | WO 2009/069442 A1 | 6/2009 |
| WO | WO 2014/021441 A1 | 2/2014 |
| WO | WO 2014/079527 A1 | 5/2014 |

OTHER PUBLICATIONS

Yamashita et al. Organic Letters (2009), 11(11), 2337-2340.*
Atzrodt et al. Angew. Chem. Int. Ed. 2007, 46, 7744-7765.*
Yamashita et al. Organic Letters (2009), 11(11), 2337-2340, Supporting_Information.*
Zhuangzhi, et al., Angewandte Chemie Int. Ed. 2010, 49, 4036-4041.
Yamashita, et al., J. Org. Chem., 2009, 74, 7481-7488.
Yamashita et al. "Synthesis of Condensed Heteroaromatic Compounds, etc ... " vol. 11, No. 11, Organic Letters, 2009 2337-2340.
Chinese Office Action dated Oct. 31, 2018.

* cited by examiner

*Primary Examiner* — Venkataraman Balasubramanian
(74) *Attorney, Agent, or Firm* — Lee & Morse, P.C.

(57) ABSTRACT

The present invention relates to a compound for an organic optoelectronic element represented by Chemical Formula 1, an element comprising the same, and a display device comprising the organic optoelectronic element (details of Chemical Formula 1 are as described in the specification).

14 Claims, 1 Drawing Sheet

[Fig. 1]
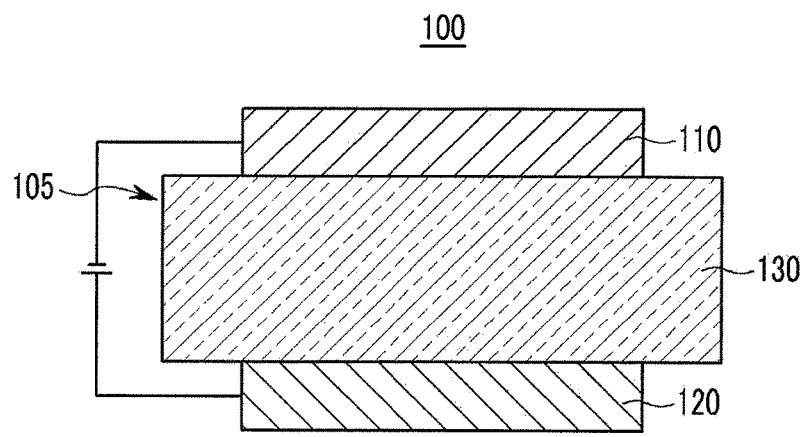
[Fig. 2]
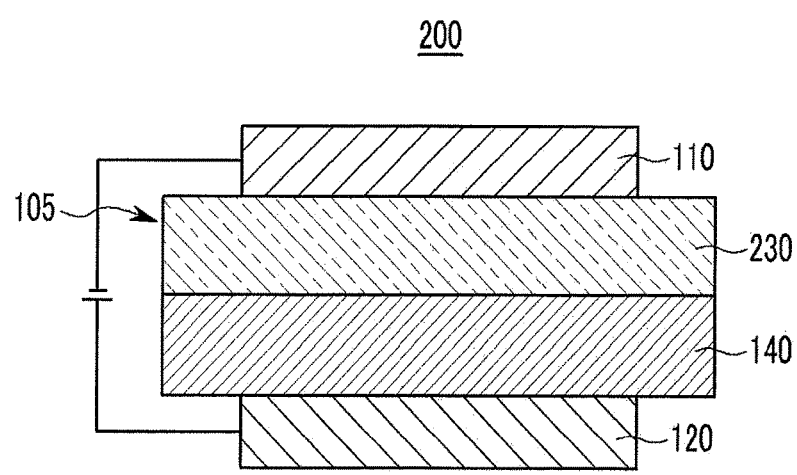

COMPOUND FOR ORGANIC OPTOELECTRONIC ELEMENT, ORGANIC OPTOELECTRONIC ELEMENT COMPRISING SAME, AND DISPLAY DEVICE

CROSS REFERENCE TO RELATED APPLICATIONS

This is the U.S. national phase application based on PCT Application No. PCT/KR2015/008245, filed Aug. 6, 2015, which is based on Korean Patent Application No. 10-2014-0152157, filed Nov. 4, 2014, the entire contents of all of which are hereby incorporated by reference.

TECHNICAL FIELD

A compound for an organic optoelectronic element, an organic optoelectronic element, and a display device are disclosed.

BACKGROUND ART

An organic optoelectronic element (organic optoelectronic device) is a device that converts electrical energy into photoenergy, and vice versa.

An organic optoelectronic element may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic element may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material and has a structure in which an organic layer is disposed between an anode and a cathode. Herein, the organic layer may include a light-emitting layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic element capable of realizing an organic optoelectronic element having high efficiency and a long lifespan.

Another embodiment provides an organic optoelectronic element including the compound for an organic optoelectronic element.

Yet another embodiment provides a display device including the organic optoelectronic element.

Technical Solution

In an embodiment of the present invention, a compound represented by Chemical Formula 1 is provided.

[Chemical Formula 1]

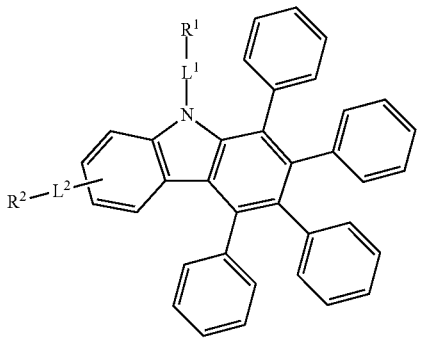

In Chemical Formula 1, $R^1$ and $R^2$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a halogen, a halogen-containing group, a cyano group, a hydroxyl group, an amino group, a nitro group, a carboxyl group, a ferrocenyl group, or a combination thereof, at least one of $R^1$ and $R^2$ is a substituted or unsubstituted nitrogen-containing C2 to C30 heterocyclic group except a carbazolyl group, and $L^1$ and $L^2$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C2 to 030 alkenylene group, a substituted or unsubstituted C2 to C30 alkynylene group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a C1 to C10 trifluoroalkyl group, or a cyano group.

In another embodiment of the present invention, an organic optoelectronic element includes an anode and a cathode facing each other and at least one organic layer disposed between the anode and the cathode, wherein the organic layer includes the compound for an organic optoelectronic element.

Yet in another embodiment of the present invention, a display device including the organic optoelectronic element is provided.

Advantageous Effects

An organic optoelectronic element having high efficiency and a long life-span may be realized.

DESCRIPTION OF THE DRAWINGS

FIGS. 1 and 2 are cross-sectional views showing various embodiments of an organic light emitting diode according to an embodiment of the present invention.

| <Description of Symbols> | |
|---|---|
| 100: organic light emitting diode | 200: organic light emitting diode |
| 105: organic layer | |
| 110: cathode | |
| 120: anode | |
| 130: light-emitting layer | 230: light-emitting layer |
| 140: hole auxiliary layer | |

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a C1 to C10 trifluoroalkyl group such as a trifluoromethyl group, or a cyano group.

In the present specification, when specific definition is not otherwise provided, "hetero" refers to one including one to three heteroatoms selected from N, O, S, P, and Si, and remaining carbons in one functional group.

In the present specification, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a cyclic substituent where all elements have p-orbitals, and these p-orbitals forms conjugation, and includes a monocyclic or fused ring polycyclic (i.e., rings sharing adjacent pairs of carbon atoms) functional group.

In the present specification, "a heterocyclic group" includes a cyclic group including at least one heteroatom selected from N, O, S, P, and Si of a cyclic compound such as aryl group, a cycloalkyl group, a fused ring, or a combination thereof and remaining carbon. When the heterocyclic group is a fused ring, each or entire ring of the heterocyclic group may include at least one heteroatom. Accordingly, the heterocyclic group has a generic concept including a heteroaryl group.

More specifically, a substituted or unsubstituted C6 to C30 aryl group and/or a substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrylene group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted carbazolyl group, a substituted or unsubstituted dibenzofuranyl group, a substituted or unsubstituted dibenzothiophenyl group, a combination thereof, or a combined fused ring of the foregoing groups, but is not limited thereto.

In the present specification, the substituted or unsubstituted nitrogen-containing C2 to C30 heterocyclic group except the carbazolyl group may be a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

In the present specification, a single bond refers to a direct bond not by carbon or a hetero atom except carbon, and specifically the meaning that L is a single bond means that a substituent linked with L directly is bound to a central core. That is, in the present specification, the single bond does not refer to methylene that is bonded via carbon.

In the present specification, hole characteristics refer to an ability to donate an electron to form a hole when an electric field is applied, and that a hole formed in the anode may be easily injected into the light-emitting layer, and a hole formed in a light-emitting layer may be easily transported into an anode and transported in the light-emitting layer due to conductive characteristics according to a highest occupied molecular orbital (HOMO) level.

In addition, electron characteristics refer to an ability to accept an electron when an electric field is applied, and that an electron formed in a cathode may be easily injected into the light-emitting layer (LUMO) level, and an electron formed in a light-emitting layer may be easily transported into a cathode and transported in the light-emitting layer due to conductive characteristics according to a lowest unoccupied molecular orbital (LUMO) level.

Hereinafter, a compound according to an embodiment is described.

In an embodiment of the present invention, a compound represented by Chemical Formula 1 is provided.

[Chemical Formula 1]

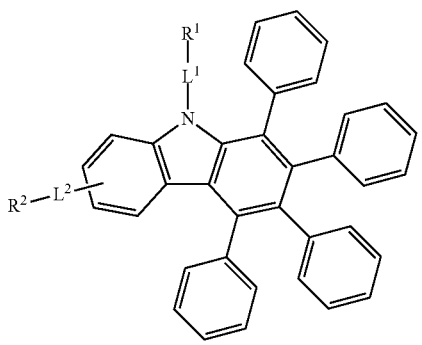

In Chemical Formula 1, $R^1$ and $R^2$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a halogen, a halogen-containing group, a cyano group, a hydroxyl group, an amino group, a nitro group, a carboxyl group, a ferrocenyl group, or a combination thereof, at least one of $R^1$ and $R^2$ is a substituted or unsubstituted nitrogen-containing C2 to C30 heterocyclic group except a carbazolyl group, and $L^1$ and $L^2$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a C1 to C10 trifluoroalkyl group, or a cyano group.

The compound for an organic optoelectronic element represented by Chemical Formula 1 has an increased molecular weight due to four phenyl groups linked with a carbazole core, and thus an increased glass transition temperature and resultantly, may be suppressed from decomposition during the deposition.

In general, a compound having an increased molecular weight and thus an increased glass transition temperature may be suppressed from decomposition during the deposition process but has a problem in terms of process stability due to an increased deposition temperature according to the increased molecular weight.

However, the compound for an organic optoelectronic element represented by Chemical Formula 1 according to the present invention has a three dimensional shape due to the four phenyl groups forming a spherically-shaped similar structure and thus may have a lower deposition temperature.

In other words, since thermal stability of the compound is simultaneously increased while the deposition temperature is lowered during the deposition process, an organic optoelectronic element manufactured by using the compound for an organic optoelectronic element according to an embodiment of the present invention may obtain high efficiency and a long life-span.

In addition, the compound may be designed to have bipolar characteristics by introducing various substituents and particularly, at least one substituent having electron characteristics into the positions of $R^1$ and $R^2$ and thus have desired efficiency and life-span.

Chemical Formula 1 may be one of Chemical Formulae I-a, I-b and I-c according to a bonding position of a substituent.

[Chemical Formula 1-a]

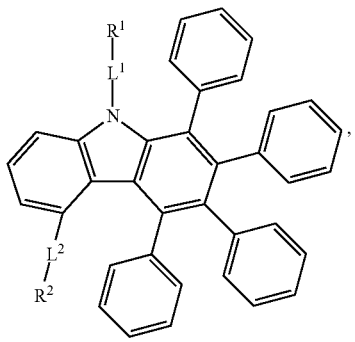

[Chemical Formula 1-b]

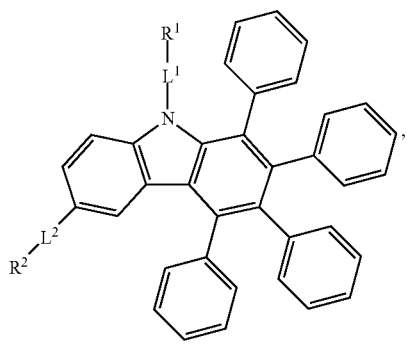

[Chemical Formula 1-c]

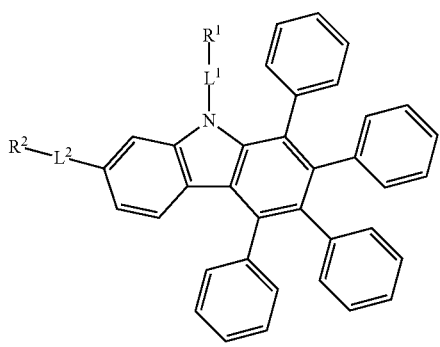

In Chemical Formulae I-a, I-b, and I-c, definitions of $R^1$, $R^2$, $L^1$, and $L^2$ are the same as described above.

Specifically, $R^1$ and $R^2$ may independently be hydrogen, deuterium, a substituted or unsubstituted C6 to C30 aryl group, a substituted or unsubstituted C2 to C30 heterocyclic group, a substituted or unsubstituted C6 to C30 arylamine group, or a combination thereof.

In addition, $L^1$ and $L^2$ may independently be a single bond, a substituted or unsubstituted C6 to C30 arylene group, or a substituted or unsubstituted C2 to C30 heteroarylene group.

More specific examples of $R^1$ and $R^2$ may be hydrogen, deuterium, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted azaphenanthrenyl group, a substituted or unsubstituted phenanthrolinyl group, or a substituted or unsubstituted phenazinyl group.

The substituted or unsubstituted nitrogen-containing C2 to C30 heterocyclic group except a carbazolyl group is a substituent having an ability to accept an electron when an electric field is applied and that an electron formed in a cathode may be easily injected into the light-emitting layer, and an electron formed in a light-emitting layer may be easily transported into a cathode and transported in the light-emitting layer due to conductive characteristics according to a lowest unoccupied molecular orbital (LUMO) level, and may be, for example a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

Specifically, it may be selected from substituted or unsubstituted groups of Group I.

[Group I]

-continued

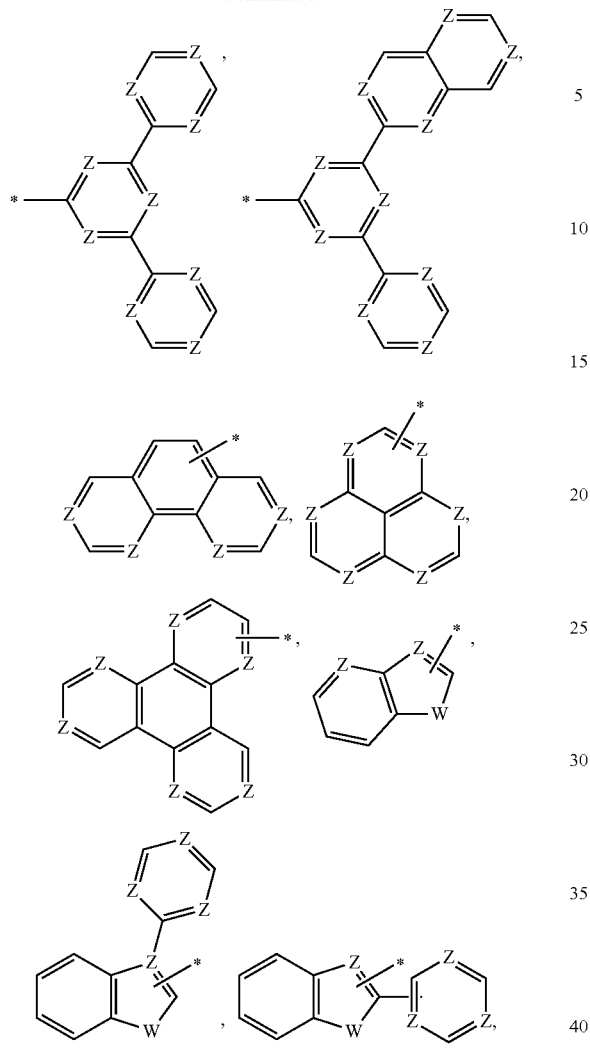

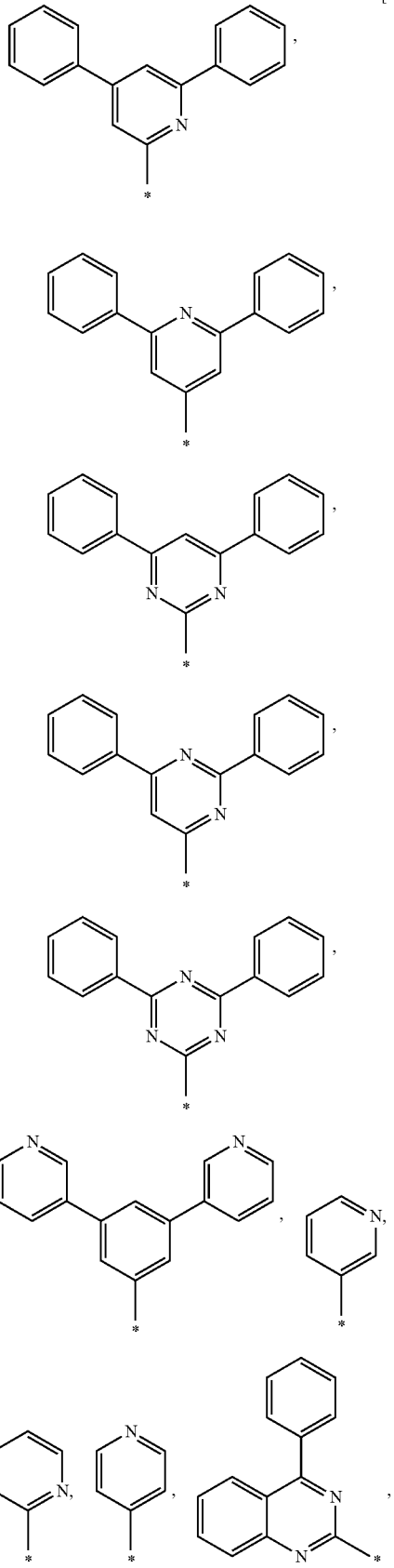

[Group I-1]

In Group I,

Z is independently N or CR$^a$, provided that at least one of Z is N, and

W is NR$^b$, O, S, SO, SO$_2$, CR$^c$R$^d$, or SiR$^e$R$^f$, wherein R$^a$ to R$^f$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a C1 to C10 trifluoroalkyl group or cyano group, and

* is a linking point and is positioned at one of elements consisting of the functional group.

The substituted or unsubstituted groups of Group I may be, for example, one of groups of Group I-1.

-continued

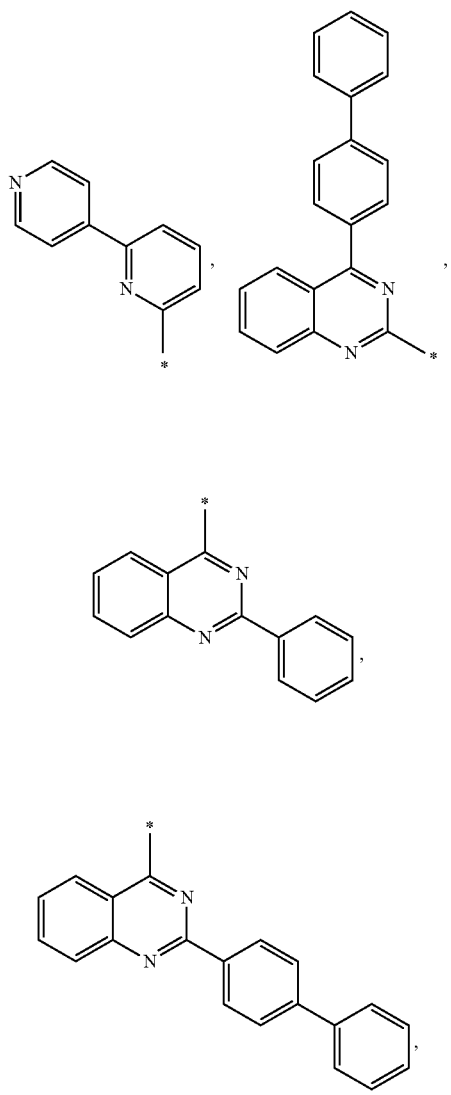

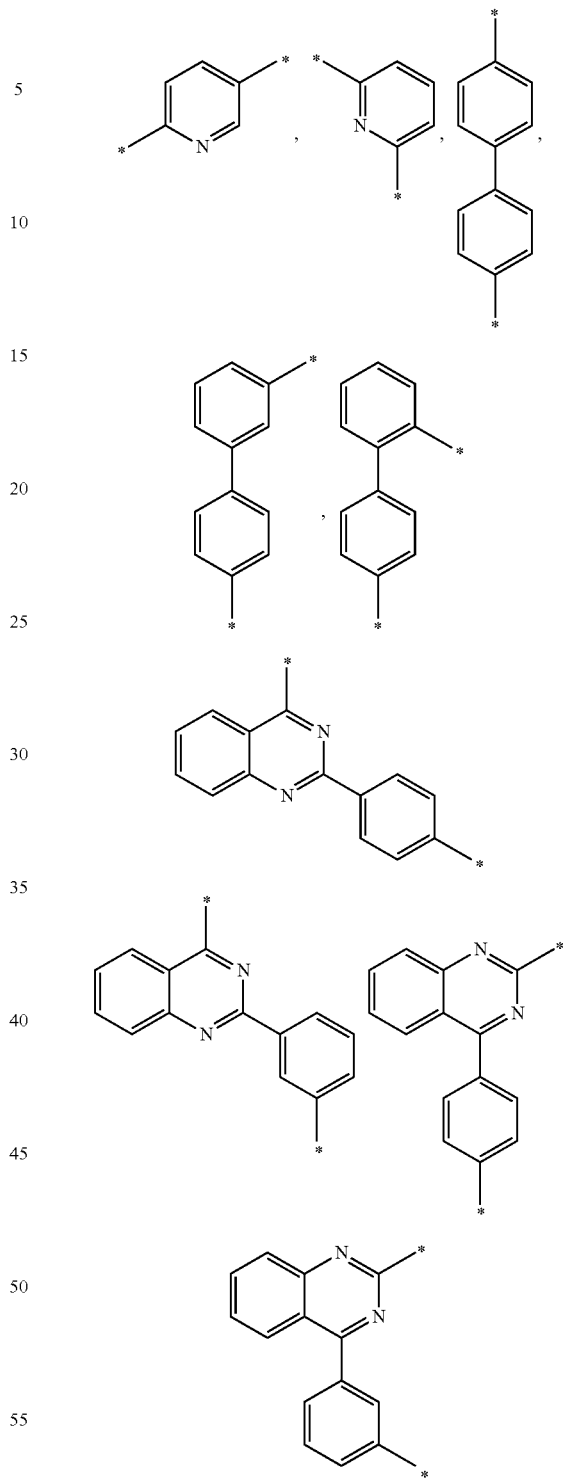

In Group I-1,

* is a linking point.

In addition, L¹ and L² may specifically be a single bond, a substituted or unsubstituted phenylene group, a substituted or unsubstituted biphenylene group, a substituted or unsubstituted naphthyl group, a substituted or unsubstituted pyridinyl group, a substituted or unsubstituted pyridmidyl group, a substituted or unsubstituted triazinyl group, a substituted or unsubstituted phenylquinazoline group, or a combination thereof. For example, it may be selected from substituted or unsubstituted groups of Group II.

[Group II]

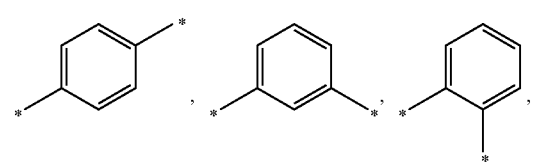

In Group II,

* is a linking point.

wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a 02 to C30 heteroaryl group, a C1 to C20 alkoxy group, a C1 to C10 trifluoroalkyl group, or a cyano group.

In one examples of the present invention, in the compound for an organic optoelectronic element, $R^1$ or $R^2$ of Chemical Formula 1 being the substituted or unsubstituted nitrogen-containing C2 to C30 heterocyclic group except a carbazolyl group may exhibit ET (electron transport) characteristics and the other of $R^1$ or $R^2$ being a substituted or unsubstituted C6 to C30 aryl group, a substituted or unsubstituted dibenzofuranyl group, or a substituted or unsubstituted dibenzothiophenyl group may exhibit HT (hole transport) characteristics.

In one example of the present invention, as the substituted or unsubstituted nitrogen-containing C2 to C30 heterocyclic group except a carbazolyl group, one of $R^1$ and $R^2$ in Chemical Formula 1 may be selected from a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, and a substituted or unsubstituted phenazinyl group; the other of $R^1$ or $R^2$ may be hydrogen, deuterium, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted dibenzothiophenyl group, a substituted or unsubstituted dibenzofuranyl group, a substituted or unsubstituted carbazole group, or a combination thereof; and $L^1$ and $L^2$ are independently a single bond or a substituted or unsubstituted C6 to C30 arylene group.

In an embodiment of the present invention, as the substituted or unsubstituted nitrogen-containing C2 to C30 heterocyclic group except a carbazolyl group, one of $R^1$ and $R^2$ in Chemical Formula 1 may be selected from a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group; the other of $R^1$ or $R^2$ may be hydrogen, deuterium, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted dibenzothiophenyl group, a substituted or unsubstituted dibenzofuranyl group, a substituted or unsubstituted carbazole group, or a combination thereof; and $L^1$ and $L^2$ are independently a single bond or a substituted or unsubstituted C6 to C30 arylene group.

The compound represented by Chemical Formula 1 may be, for example compounds below, but is not limited thereto.

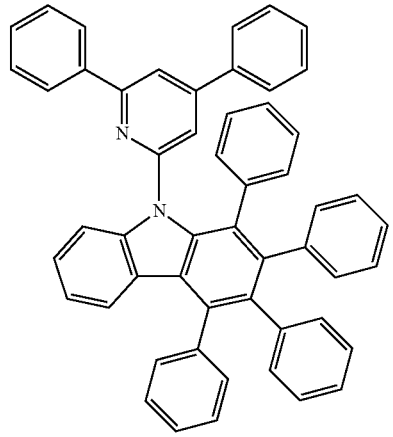

[A-1]

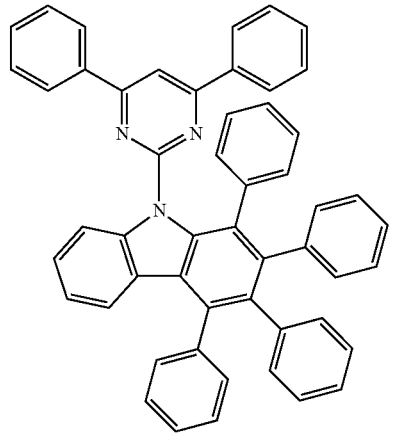

[A-2]

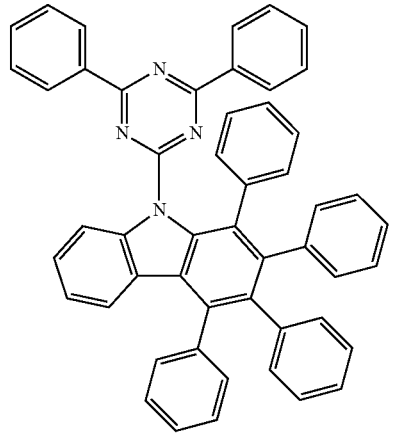

[A-3]

[A-4]
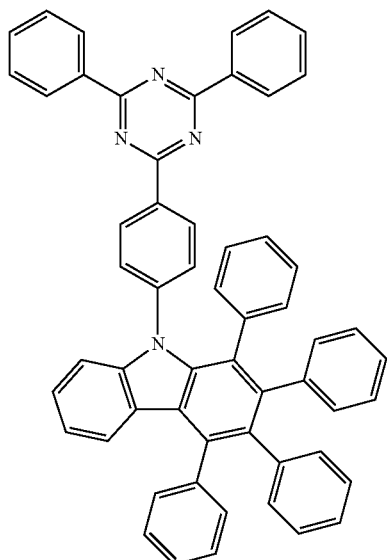
[A-6]
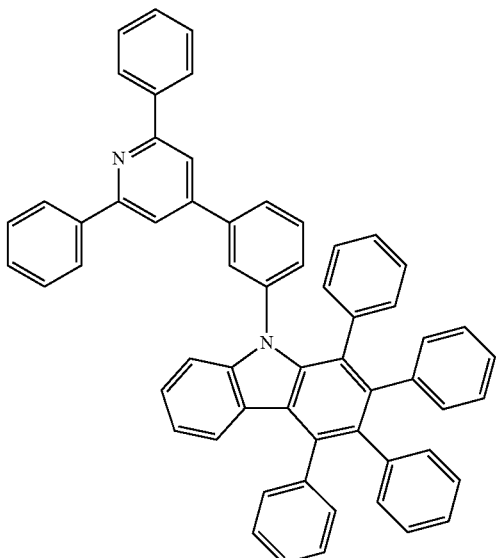
[A-5]
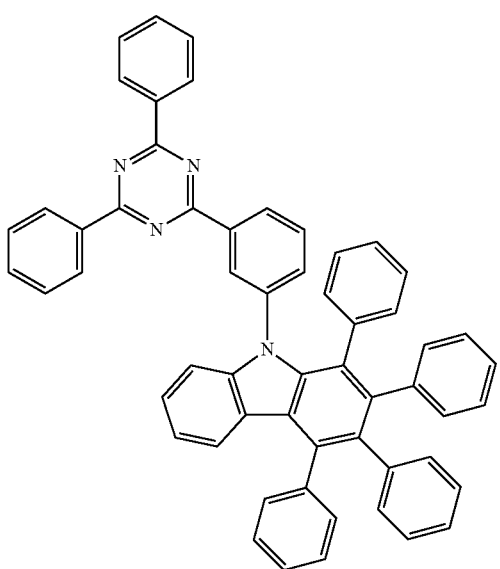
[A-7]
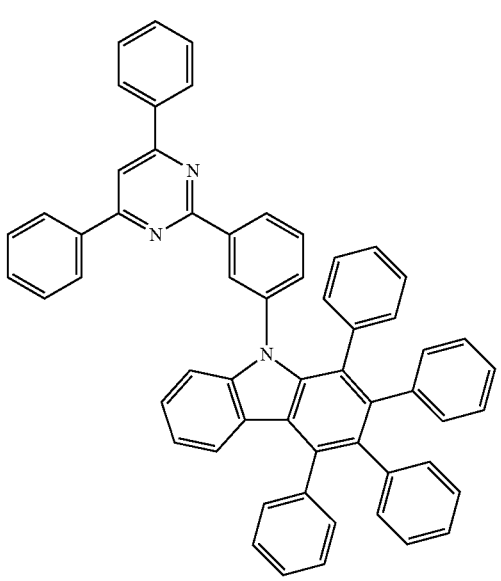

[A-8]
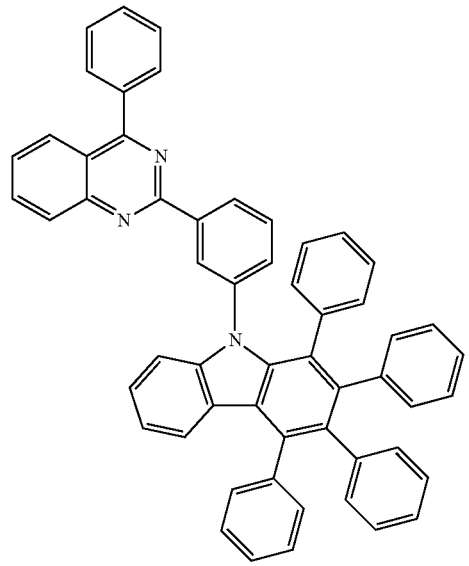
[A-9]
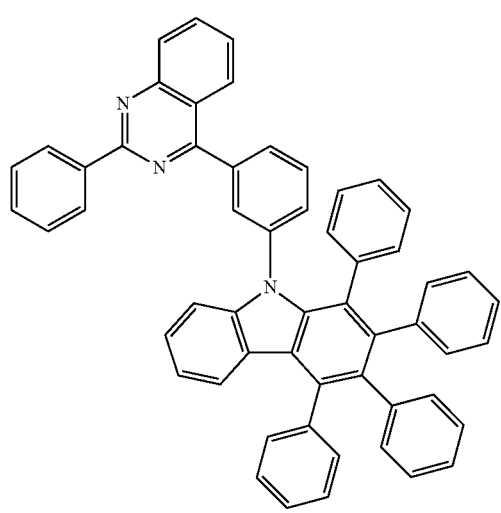
[A-10]
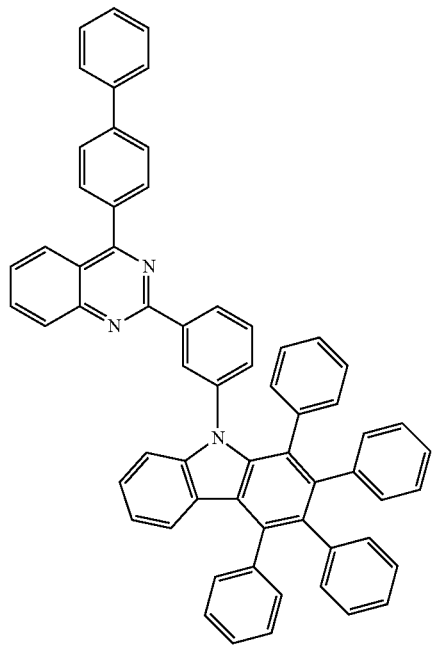
[A-11]
[A-12]
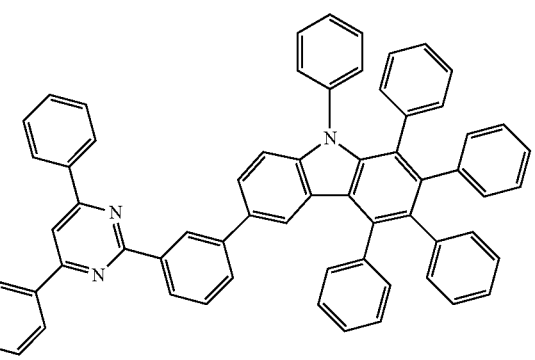

-continued
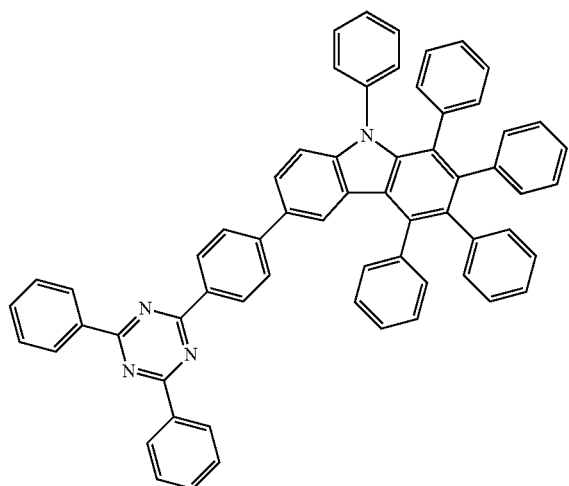
[A-13]
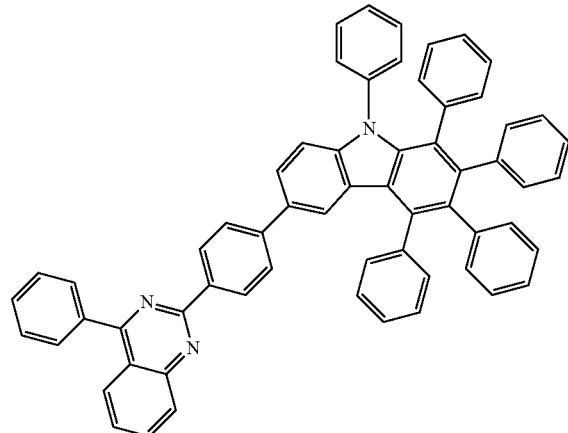
[A-16]
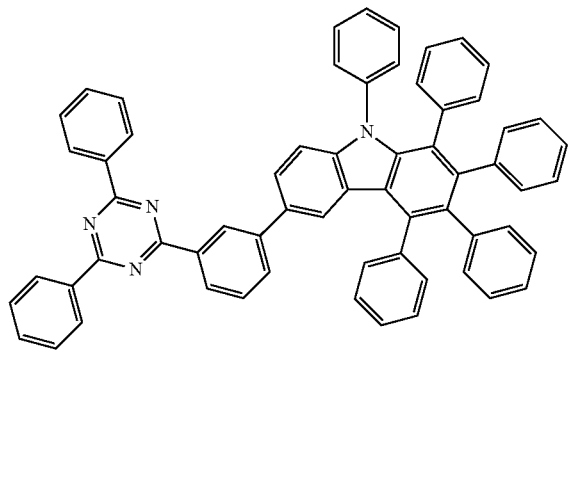
[A-14]
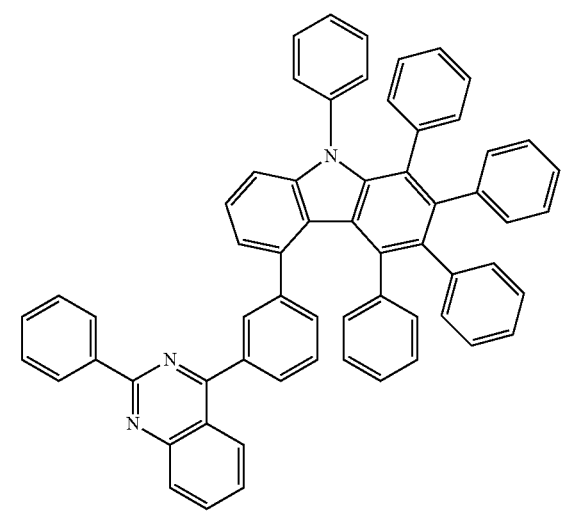
[A-17]
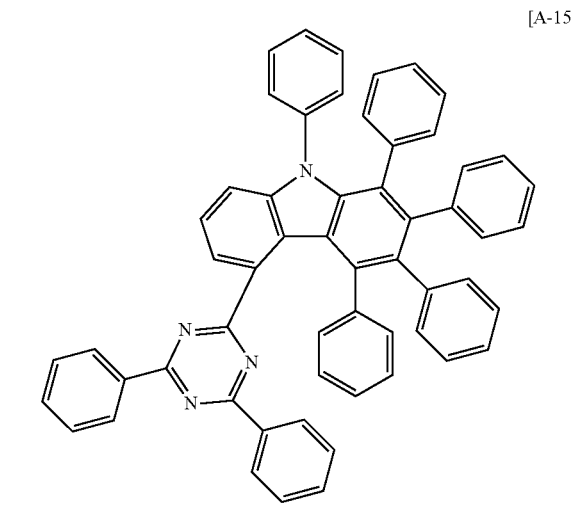
[A-15]
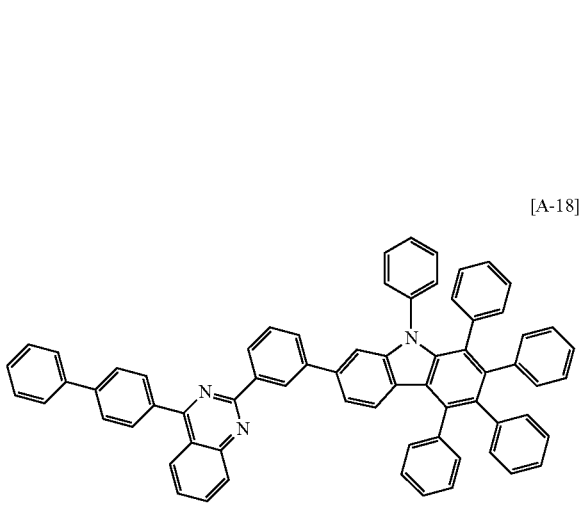
[A-18]

[A-19]
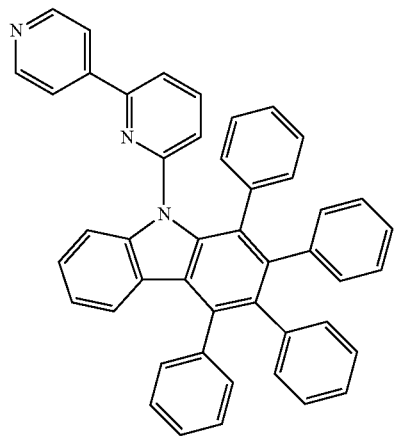
[A-22]
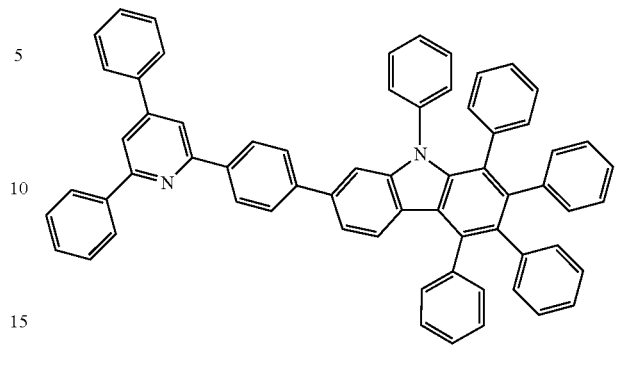
[A-20]
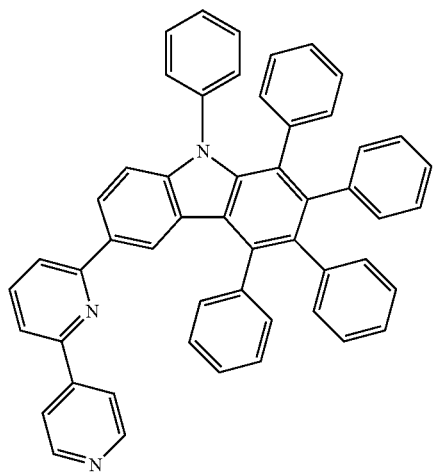
[A-23]
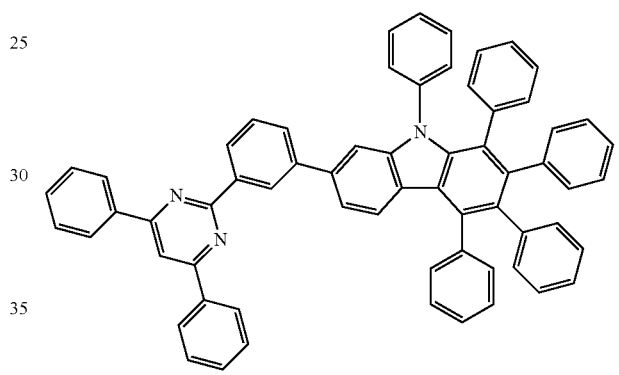
[A-21]
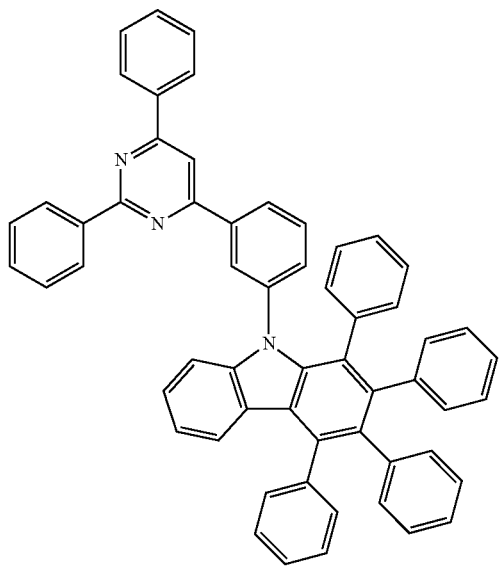
[A-24]
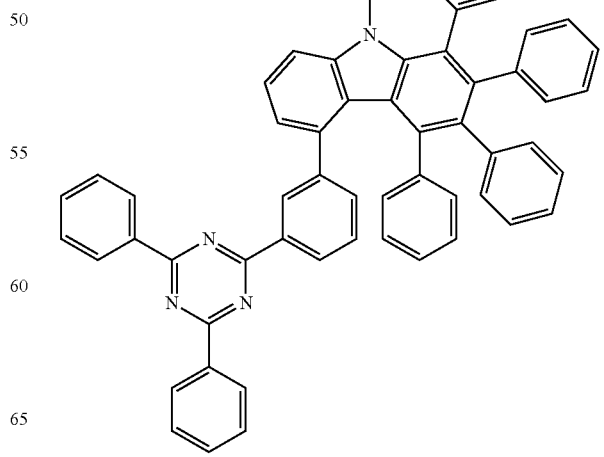

[A-25]
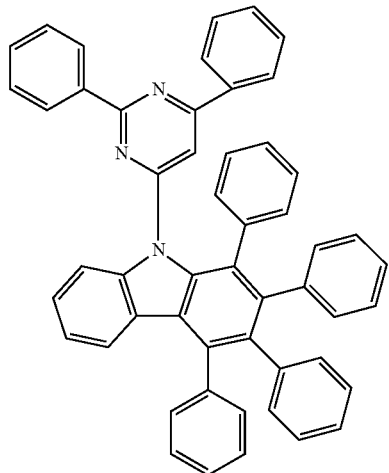
[A-28]
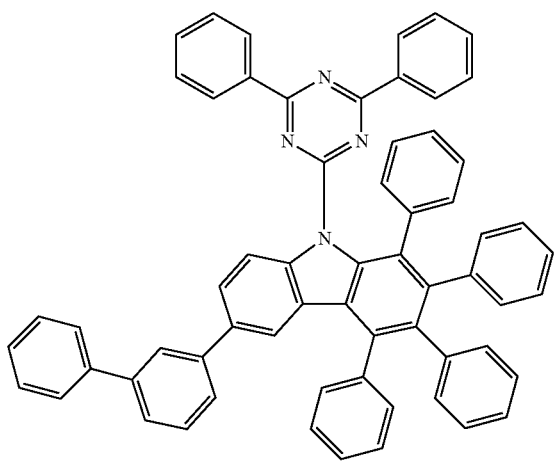
[A-26]
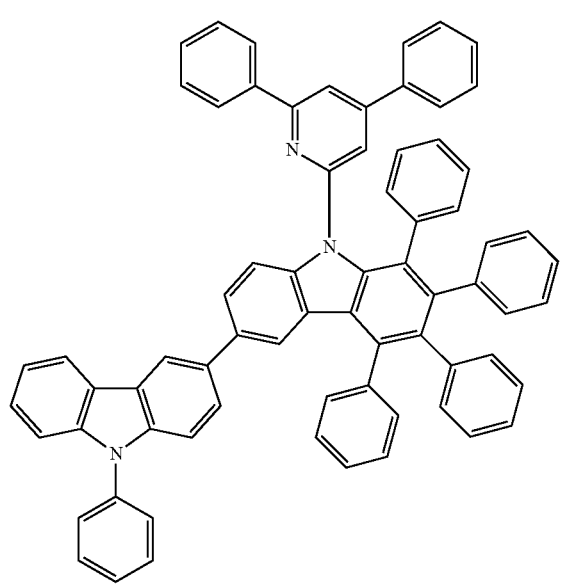
[A-27]
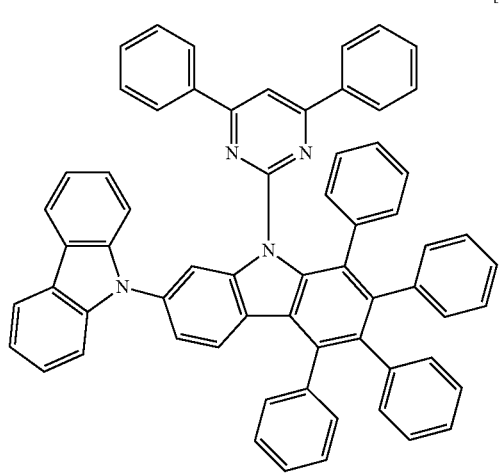
[A-29]
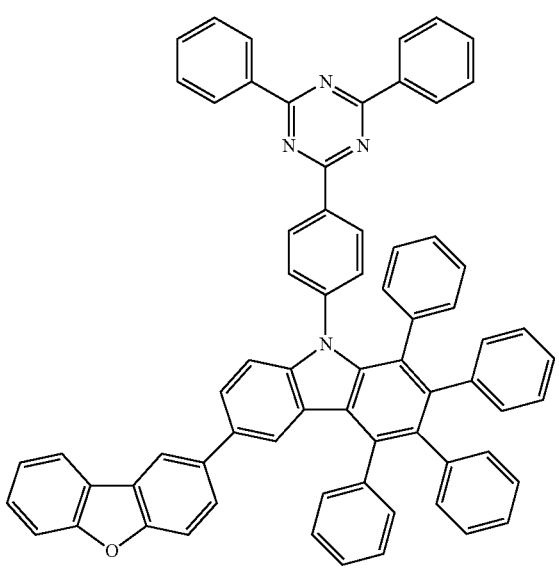

[A-30]
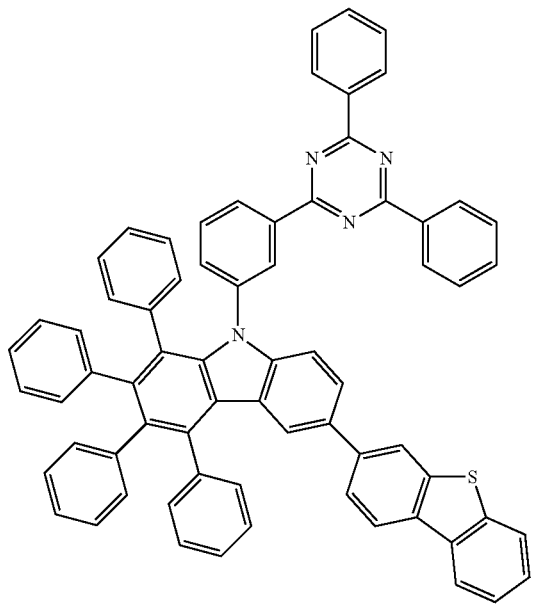
[A-31]
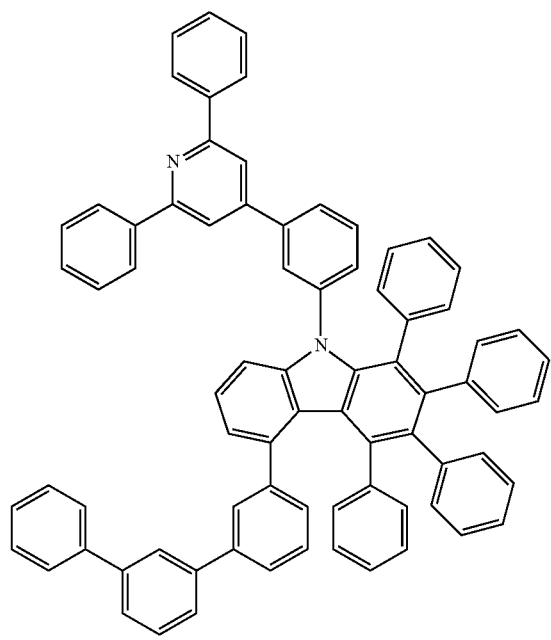
[A-32]
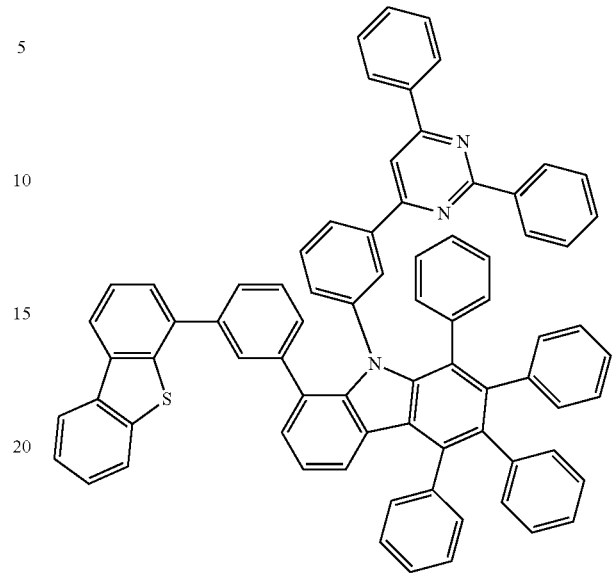
[A-33]
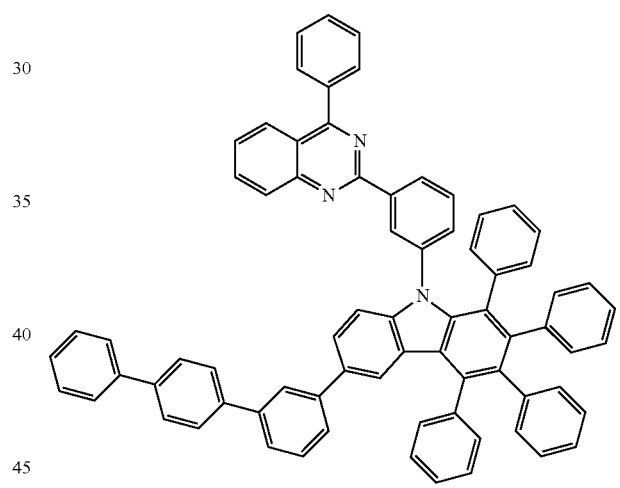
[A-34]
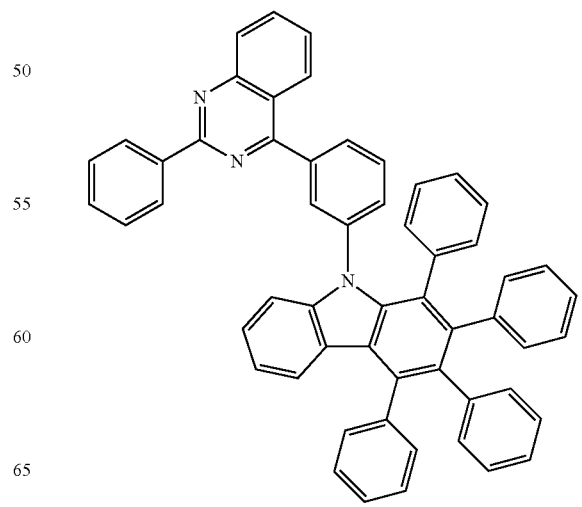

[A-35]
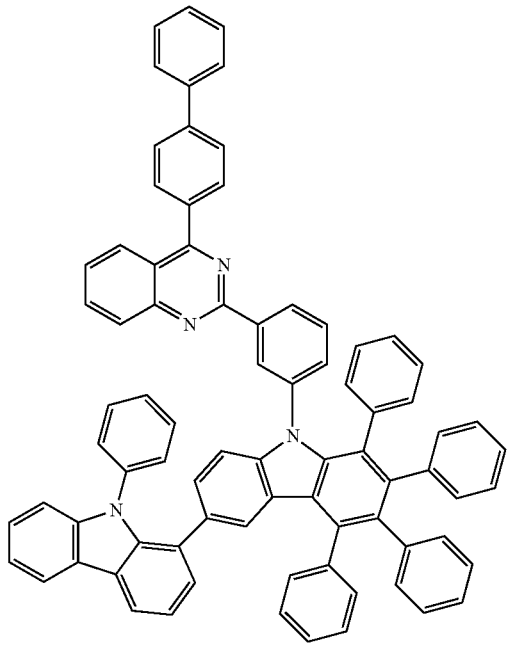
[A-37]
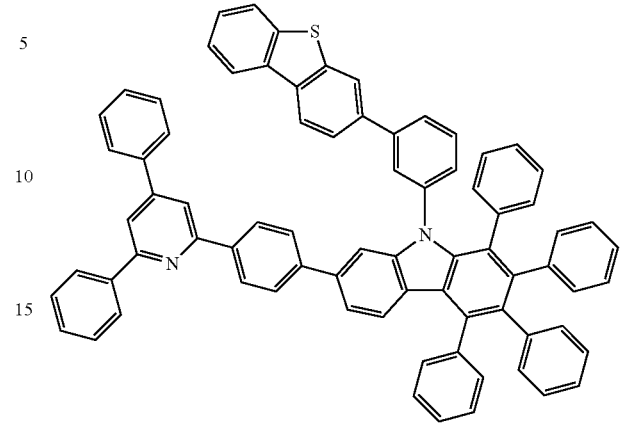
[A-38]
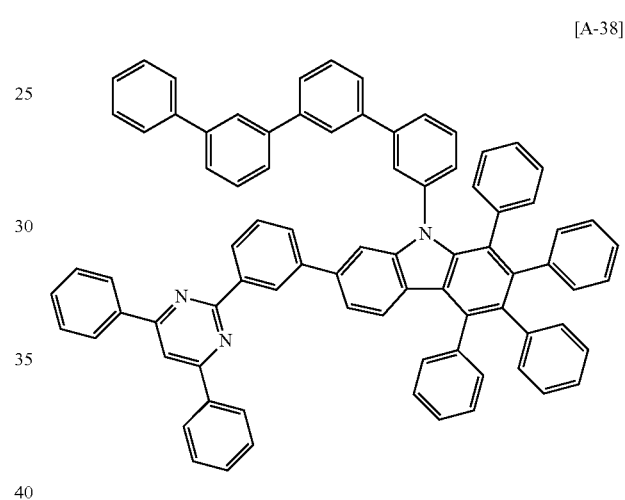
[A-36]
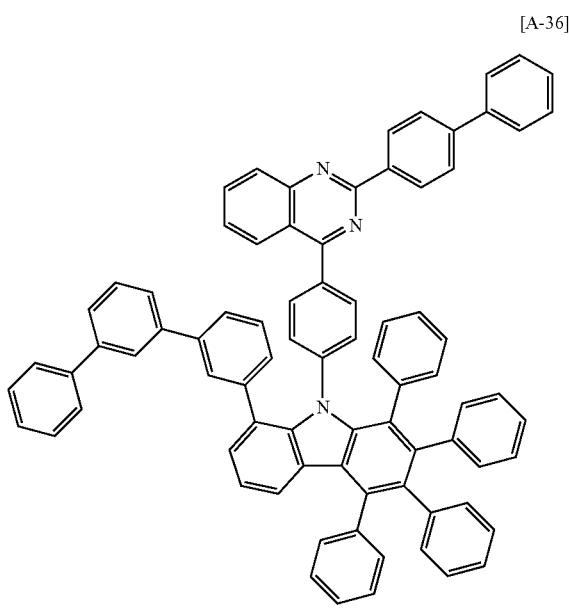
[A-39]
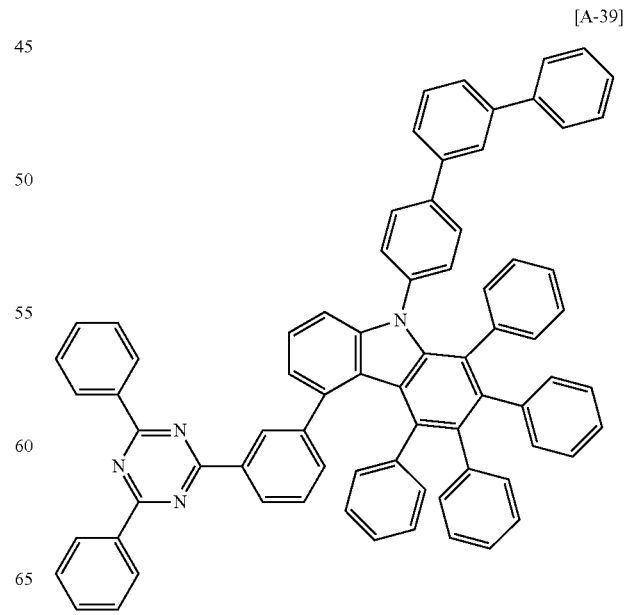

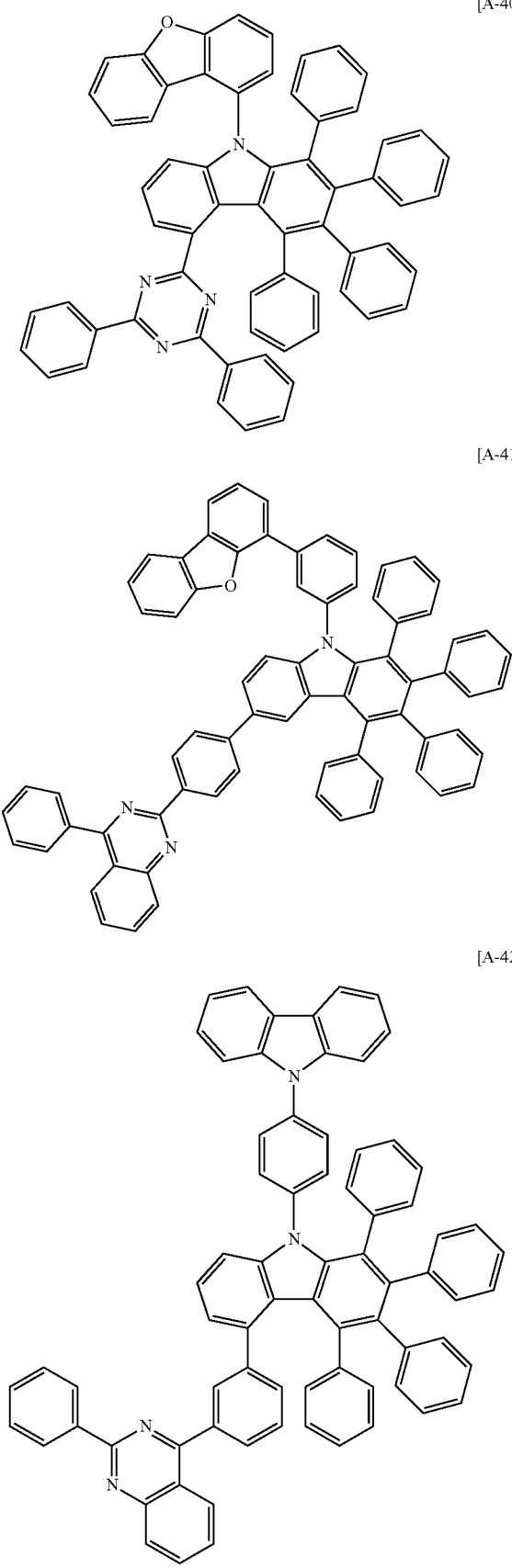
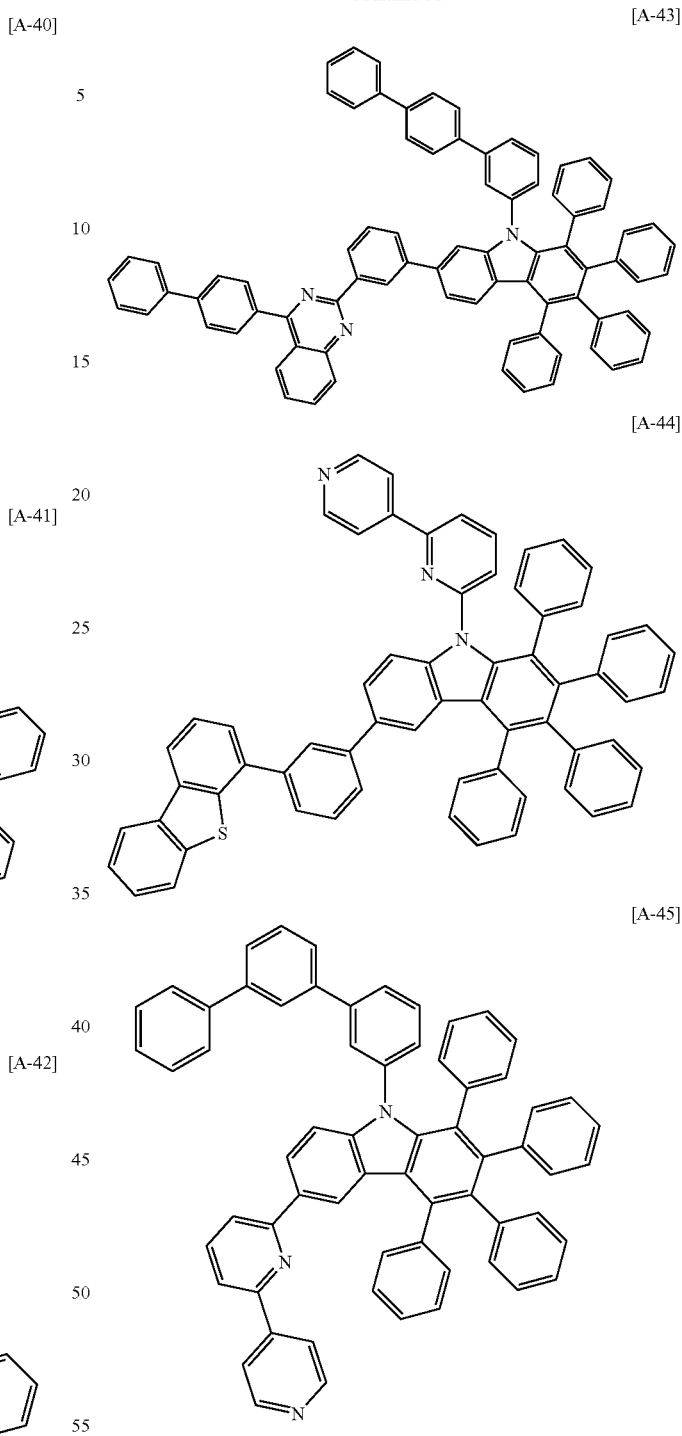

Hereinafter, an organic optoelectronic element including the organic compound is described.

In another embodiment of the present invention, an organic optoelectronic element includes an anode and a cathode facing each other and at least one organic layer disposed between the anode and the cathode, wherein the organic layer includes the compound for an organic optoelectronic element.

The organic layer may include a light-emitting layer and the light-emitting layer may include the compound for an organic optoelectronic element of the present invention.

Specifically, the compound for an organic optoelectronic element may be included as a host of the light-emitting layer.

In addition, in an organic optoelectronic element according to an embodiment of the present invention, the organic layer includes at least one auxiliary layer selected from a hole injection layer, a hole transport layer, an auxiliary hole transport layer, an auxiliary electron transport layer, an electron transport layer, and an electron injection layer, wherein the auxiliary layer includes the compound for an organic optoelectronic element.

The organic optoelectronic element may be any device to convert electrical energy into photoenergy and vice versa without particular limitation, and may be, for example an organic photoelectric diode, an organic light emitting diode, an organic solar cell, and an organic photo conductor drum.

Herein, an organic light emitting diode as one example of an organic optoelectronic element is described referring to drawings.

FIGS. 1 and 2 are cross-sectional views showing an organic light emitting diode according to an embodiment.

Referring to FIG. 1, an organic light emitting diode 100 according to an embodiment includes an anode 120 and a cathode 110 and an organic layer 105 between the anode 120 and the cathode 110.

The anode 120 may be made of a conductor having a large work function to help hole injection, and may be for example a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO$_2$/Al, LiF/Ca, LiF/Al, and BaF$_2$/Ca, but is not limited thereto.

The organic layer 105 may include a light-emitting layer 130 including the compound for an organic optoelectronic element.

The light-emitting layer 130 may include, for example the compound for an organic optoelectronic element alone, at least two kinds of the compound for an organic optoelectronic element, or a mixture of the compound for an organic optoelectronic element and other compounds. In case of the mixture of the compound for an organic optoelectronic element and other compounds, for example they may be included as a host and a dopant, and the compound for an organic optoelectronic element may be included, for example as a host. The host may be, for example a phosphorescent host or a fluorescent host, for example a phosphorescent host.

When the compound is included as a host, the dopant may be an inorganic, organic, or organic/inorganic compound and may be selected from known dopants.

Referring to FIG. 2, an organic light emitting diode 200 further includes a hole auxiliary layer 140 in addition to a light-emitting layer 230. The hole auxiliary layer 140 increases hole injection and/or hole mobility and blocks electrons between the anode 120 and the light-emitting layer 130. The hole auxiliary layer 140 may be for example a hole transport layer, a hole injection layer, and/or an electron blocking layer, and may include at least one layer.

Even not shown in FIGS. 1 and 2, the organic layer 105 may further include an electron injection layer, an electron transport layer, an auxiliary electron transport layer, a hole transport layer, an auxiliary hole transport layer, a hole injection layer, or a combination thereof. The compound for an organic optoelectronic element of the present invention may be included in these organic layers. The organic light emitting diodes 100 and 200 may be manufactured by forming an anode or a cathode on a substrate, forming an organic layer using a dry coating method such as evaporation, sputtering, plasma plating, and ion plating; or a wet coating method such as spin coating, dipping, and flow coating, and forming a cathode or an anode.

The organic light emitting diode may be applied to an organic light emitting display device.

Hereinafter, the embodiments are illustrated in more detail with reference to examples. These examples, however, are not in any sense to be interpreted as limiting the scope of the invention.

(Preparation of Compound for Organic Optoelectronic Device)

The compound as one specific examples of the present invention was synthesized through the following steps.

Hereinafter, compounds used in Examples and Synthesis Examples were purchased from Sigma-Aldrich Co. Ltd. or TCI Inc. as far as there in no particular comment.

Synthesis Example 1: Synthesis of Intermediate L-1

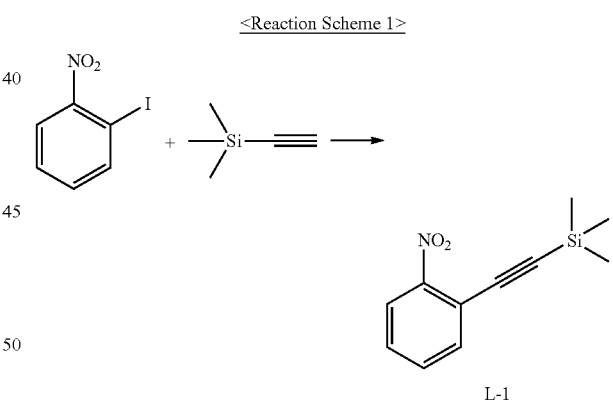

50 g (200.80 mmol) of 1-ioide-2-nitrobenzene was dissolved in 800 ml of tetrahydrofuran in a 2000 mL flask. 21.69 ml (220.87 mmol) of ethynyltrimethylsilane was slowly dropped through a dropping funnel under a nitrogen flow. When the ethynyltrimethylsilane was completely added thereto, the mixture was stirred for 3 hours at room temperature to complete a reaction. The tetrahydrofuran was condensed with a distiller and purified through column (dichloromethane:hexane=1:9) to obtain Intermediate L-1 (38 g, 86%).

calcd. C11H13NO2Si: C, 60.24; H, 5.97; N, 6.39; O, 14.59; Si, 12.81; found: C, 60.12; H, 5.88; N, 6.31; O, 14.64; Si, 12.87.

Synthesis Example 2: Synthesis of Intermediate L-2

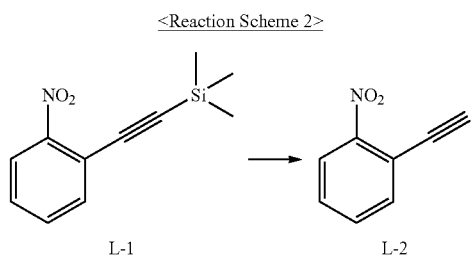

38 g (173.27 mmol) of Intermediate L-1 was stirred with 500 ml of methanol in a 1000 mL flask. 24 g (173.27 mmol) of potassium carbonate was added thereto, and the mixture was stirred for 10 minutes at room temperature to complete a reaction. The reactant was filtered, water and ethylacetate were respectively added thereto in an amount of 500 ml after removing the potassium carbonate, and the water was separated through an extraction. The separated organic solvent was removed through a distiller to obtain Intermediate L-2 (25.1 g, 98%).

calcd. $C_8H_5NO_2$: C, 65.31; H, 3.43; N, 9.52; O, 21.75; found: C, 65.25; H, 3.47; N, 9.56; O, 21.58.

Synthesis Example 3: Synthesis of Intermediate L-3

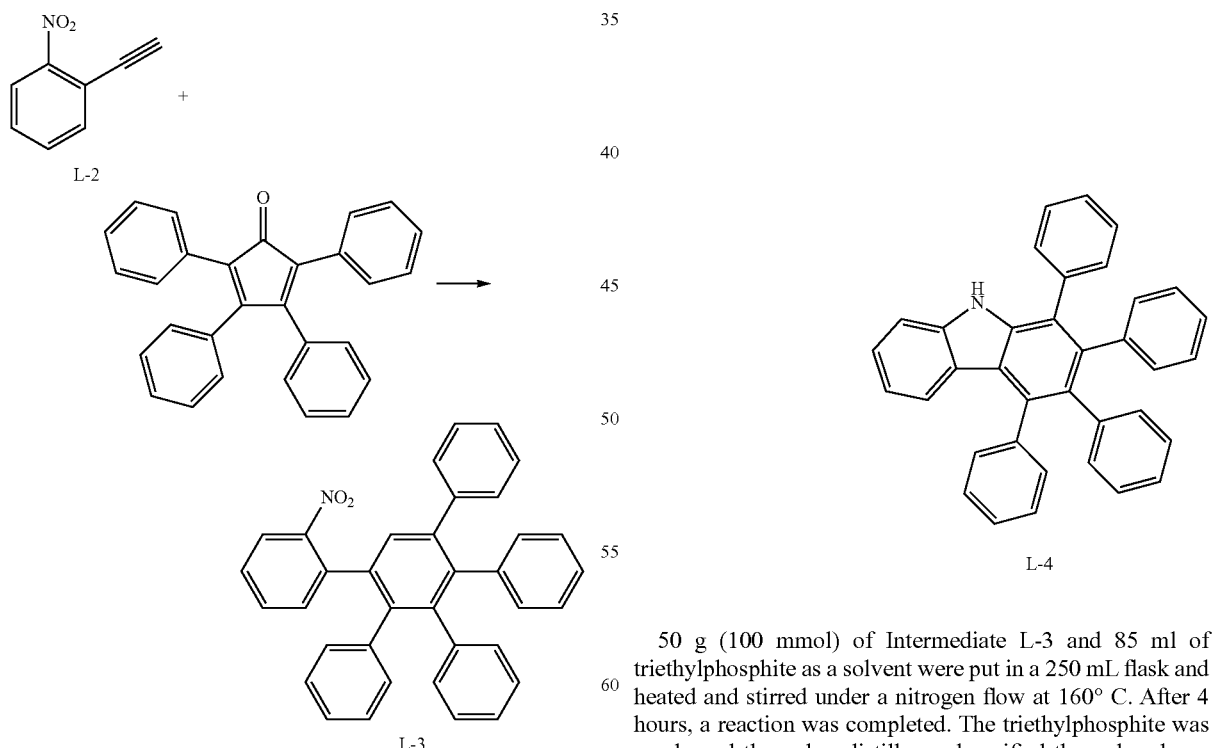

50 g (130.05 mmol) of 2,3,4,5-tetraphenylcyclopenta-2,4-diene and 21.05 g (143.05 mmol) of Intermediate L-2 were put in a 250 mL flask, and 150 ml of xylene was added thereto. The mixture was heated and stirred under a nitrogen flow at 180° C. After 2 hours, a reaction was completed. After completing the reaction, the reactant was slowly dropped to 1000 mL of methanol to produce a solid. The mixture having the solid was stirred for 2 hours and then, filtered to obtain Intermediate L-3 (50.28 g, 77%).

calcd. $C_{36}H_{25}NO_2$: C, 85.86; H, 5.00; N, 2.78; O, 6.35; found: C, 85.77; H, 5.11; N, 2.67; O, 6.38.

Synthesis Example 4: Synthesis of Intermediate L-4

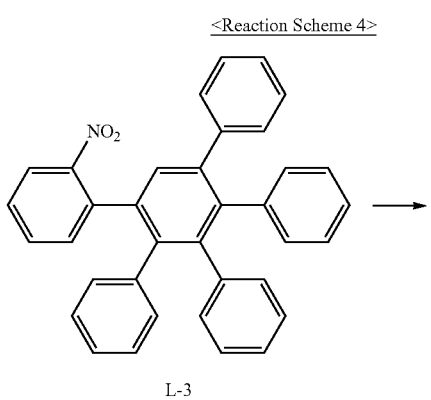

50 g (100 mmol) of Intermediate L-3 and 85 ml of triethylphosphite as a solvent were put in a 250 mL flask and heated and stirred under a nitrogen flow at 160° C. After 4 hours, a reaction was completed. The triethylphosphite was condensed through a distiller and purified through column (dichloro methane:hexane=1:9) to obtain Intermediate L-4 (28 g, 60%).

calcd. $C_{36}H_{25}N$: C, 91.69; H, 5.34; N, 2.97; found: C, 91.61; H, 5.39; N, 2.95.

Synthesis Example 5: Synthesis of Intermediate L-5

<Reaction Scheme 5>

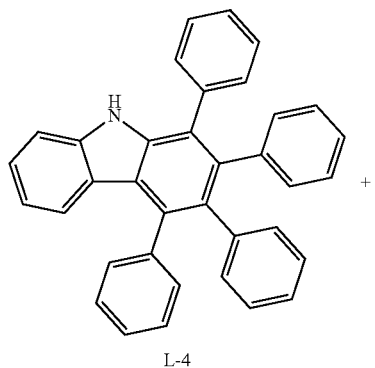

L-4

+

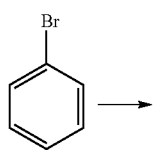

→

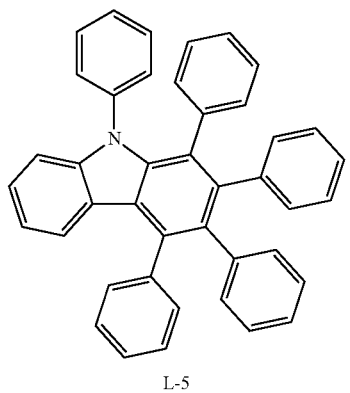

L-5

20 g (42.41 mmol) of Intermediate L-4, 8.66 g (55.13 mmol) of bromobenzene, 5.30 g (55.13 mmol) of sodium t-butoxide, 1.165 g (1.27 mmol) of Pd(dba)$_2$, 1.86 mL of tri t-butylphosphine (50% in toluene), and 170 ml of the toluene were put in a 500 mL flask and stirred at 130° C. under a nitrogen flow. After 15 hours, a reaction was completed. The obtained mixture was added to 1000 mL of methanol to crystallize a solid, and the solid was filtered, dissolved in toluene, filtered again with silica gel/Celite, and recrystallized with methanol after removing an appropriate amount of an organic solvent to obtain Intermediate L-5 (19.8 g, 85%).

calcd. C42H29N: C, 92.11; H, 5.34; N, 2.56; found: C, 91.61; H, 5.39; N, 2.65.

Synthesis Example 6: Synthesis of Intermediate L-6

<Reaction Scheme 6>

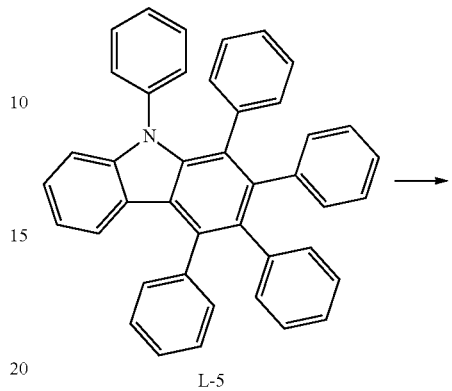

L-5

→

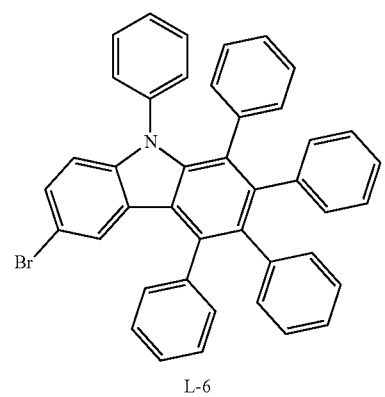

L-6

20 g (36.52 mmol) of Intermediate L-5, 6.82 g (38.34 mmol) of N-bromosuccinimide, and 120 ml of dichloromethane as a solvent were put in a 250 mL flask and stirred under a nitrogen flow at room temperature. After 4 hours, a reaction was completed. After completing the reaction, water was added thereto to extract and separate an organic solvent, 1000 mL of methanol was added to the organic solvent, and a crystallized solid was filtered to obtain Intermediate L-6 (19 g, 83%).

calcd. C42H28BrN: C, 80.51; H, 4.50; Br, 12.75; N, 2.24; found: C, 80.41; H, 4.58; Br, 12.70; N, 2.32.

Synthesis Example 7: Synthesis of Intermediate L-7

<Reaction Scheme 7>

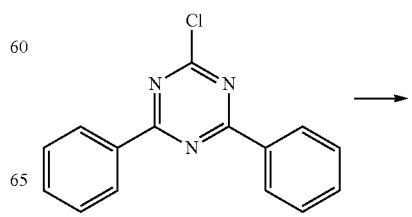

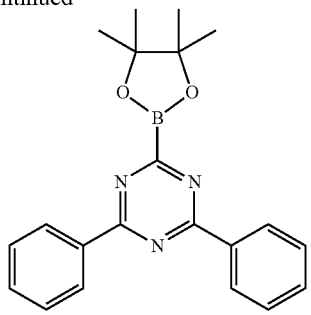

L-7

50.0 g (188.77 mmol) of Intermediate, 2-chloro-4,6-diphenyl-1,3,5-triazine, 71.14 g (280.15 mmol) of bis(pinacolato)diboron, 54.99 g (560.31 mmol) of potassium acetate, 9.15 g (11.21 mmol) of Pd(dppf)Cl$_2$, 12.57 g (44.82 mmol) of tricyclohexylphosphine, and 650 mL of dimethyl formamide were put in a 1000 ml flask and then, heated and refluxed under a nitrogen flow for 12 hours. The obtained mixture was added to 1500 mL of methanol, and a crystallized solid was filtered, dissolved in dichloromethane, filtered again with silica gel/Celite, and recrystallized after removing an appropriate amount of the organic solvent to obtain Compound L-7 (53.60 g, 80%).

calcd. C$_{21}$H$_{22}$BN$_3$O$_2$: C, 70.21; H, 6.17; B, 3.01; N, 11.70; O, 8.91; found: C, 70.11; H, 6.18; B, 3.02; N, 11.76; O, 8.99.

Synthesis Example 8: Synthesis of Intermediate L-8

<Reaction Scheme 8>

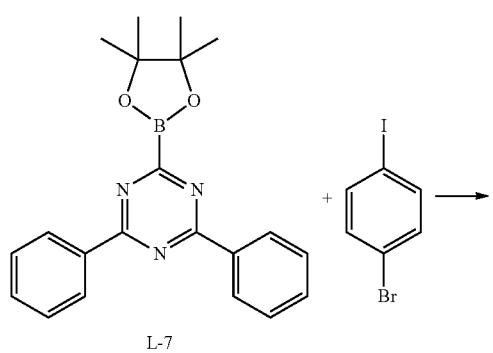

30.0 g (83.51 mmol) of Intermediate L-7, 28.35 g (100.21 mmol) of 1-bromo-4-iodebenzene, 23.08 g (167.02 mmol) of potassium carbonate, and 4.83 g (4.18 mmol) of Pd(PPh$_3$)$_4$ (tetrakis(triphenylphosphine)palladium (0)) were added to 350 mL of tetrahydrofuran and 100 mL of water in a 1000 ml flask, and the mixture was heated and refluxed under a nitrogen flow for 10 hours. The resultant was added to 1500 mL of methanol, and a crystallized solid was filtered, dissolved in dichloromethane, filtered again with silica gel/Celite, and recrystallized with methanol after removing an appropriate amount of the organic solvent to obtain Compound L-8 (37.3 g, 83%).

calcd. C$_{21}$H$_{14}$BrN$_3$: C, 64.96; H, 3.63; Br, 20.58; N, 10.82; found: C, 64.91; H, 3.58; Br, 20.63; N, 10.86.

Synthesis Example 9: Synthesis of Intermediate L-9

<Reaction Scheme 9>

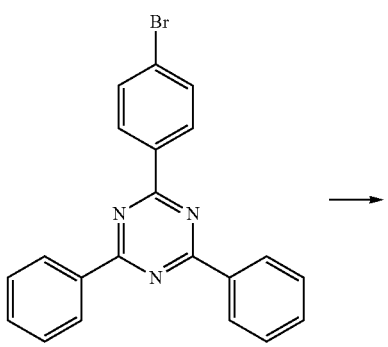

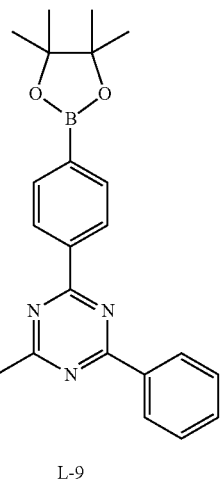

L-9

30.0 g (77.27 mmol) of Intermediate L-8, 29.43.g (115.90 mmol) of bis(pinacolato) diboron, 22.75 g (231.80 mmol) of potassium acetate, and 3.15 g (3.86 mmol) of Pd(dppf)Cl$_2$ were added to 300 mL of toluene in a 1000 ml flask, and the mixture was heated and refluxed under a nitrogen flow for 10 hours. The resultant was added to 1500 mL of methanol, and a crystallized solid was filtered, dissolved in dichloromethane, filtered again with silica gel/Celite, and recrystallized with hexane after removing an appropriate amount of the organic solvent to obtain Compound L-9 (26.4 g, 78%).

calcd. C$_{27}$H$_{26}$BN$_3$O$_2$: C, 74.49; H, 6.02; B, 2.48; N, 9.65; O, 7.35; found: C, 74.42; H, 6.12; B, 2.40; N, 9.58; O, 7.41.

Synthesis of Intermediates L-10, L-11, L-12, and L-13

Intermediates L-10, L-11, L-12, and L-13 as specific examples of a compound according to the present invention were synthesized according to the same method as the method of synthesizing Intermediates L-7, L-8, and L-9 of Synthesis Examples 7, 8, and 9 (three basic reactions: a Suzuki reaction, Boration reaction of Br, and Boration reaction of Cl)
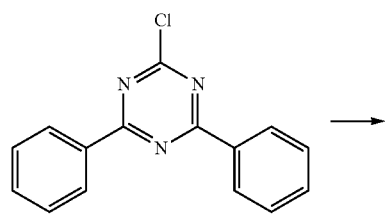
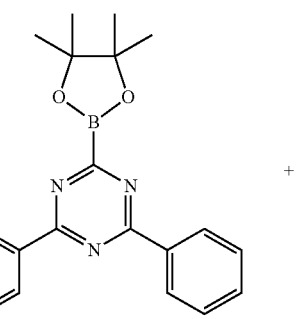
+
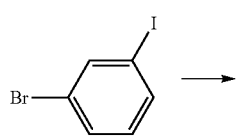
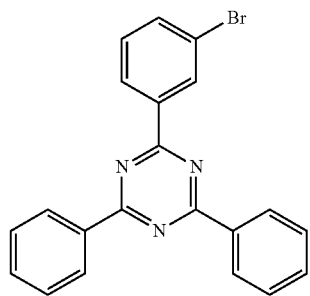
L-10
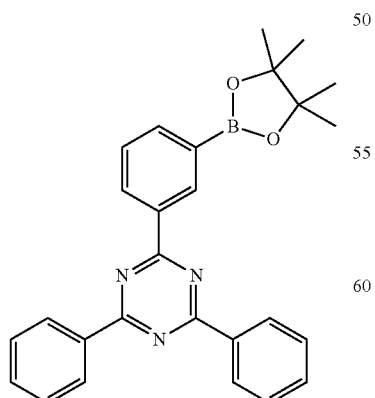
L-11
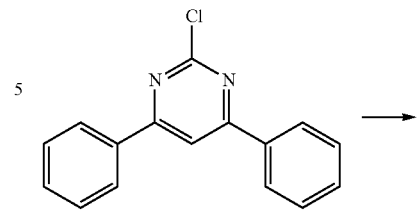
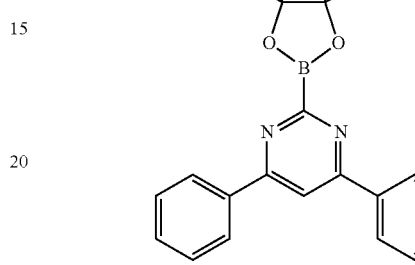
+
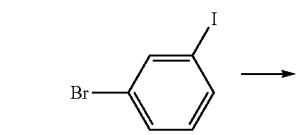
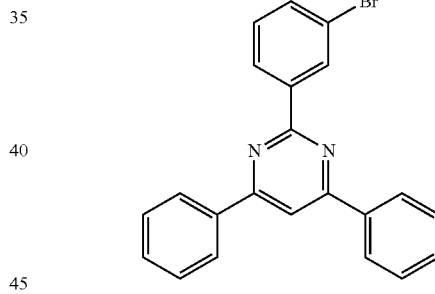
L-12
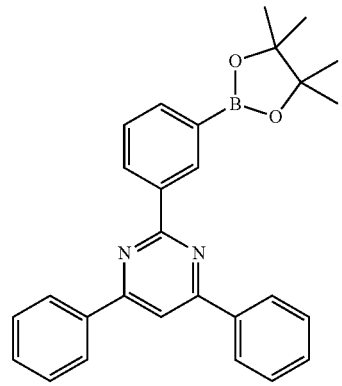
L-13

Example 1: Synthesis of Example A-4

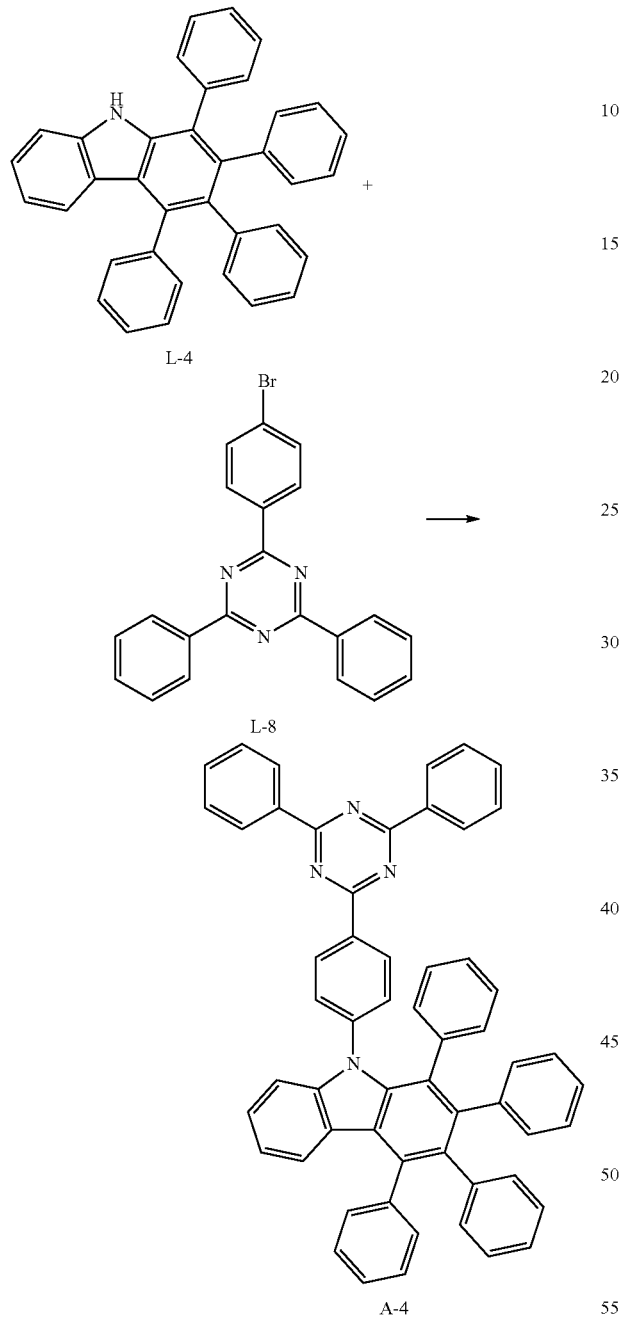

Example 2: Synthesis of Example A-5

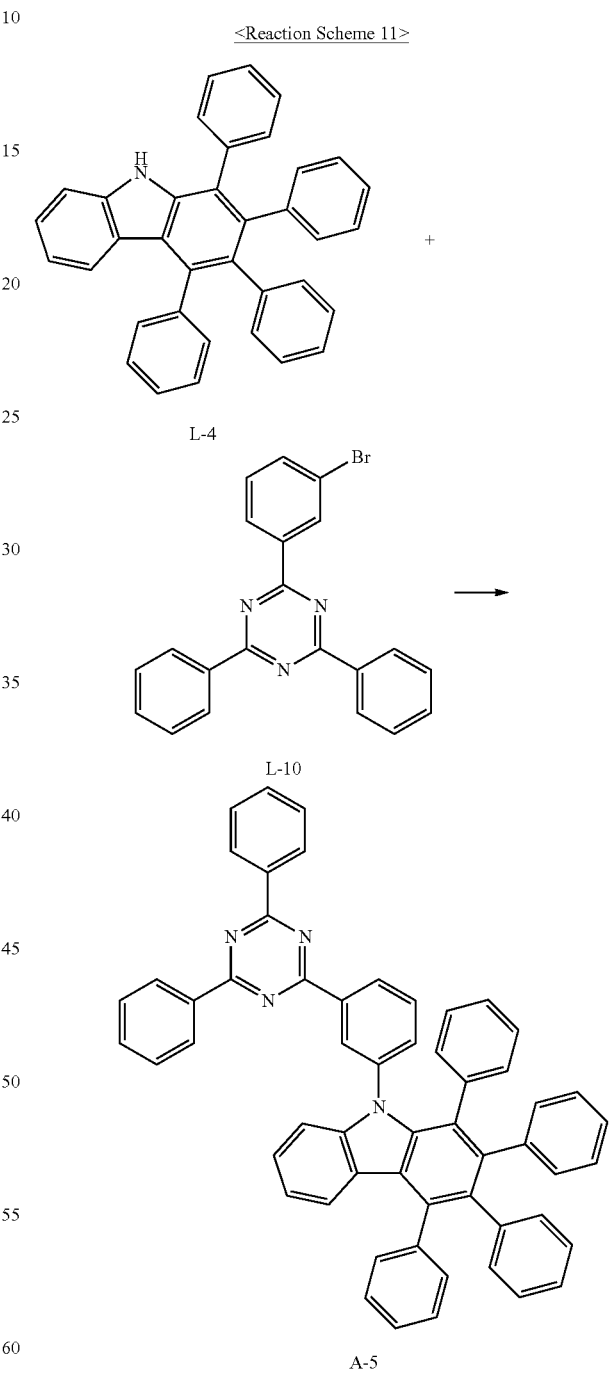

10 g (21.20 mmol) of Intermediate L-4, 8.64 g (22.27 mmol) of Intermediate L-8, 2.65 g (27.57 mmol) of sodium t-butoxide, 0.58 g (0.64 mmol) of Pd(dba)$_2$, 0.93 mL of tri t-butylphosphine (50% in toluene), and 85 ml of the toluene were put in a 500 mL flask and then, heated and stirred at 130° C. under a nitrogen flow. After 15 hours, a reaction was completed. The resultant was added to 500 mL of methanol, and a crystallized solid was filtered, dissolved in toluene, filtered again with silica gel/Celite, and recrystallized with methanol after removing an appropriate amount of an organic solvent to obtain Intermediate A-4 (13.0 g, 79%). An elemental analysis result of the produced compound is as follows.

calcd. C57H38N4: C, 87.89; H, 4.92; N, 7.19; found: C, 87.81; H, 4.99; N, 7.23;

10 g (21.20 mmol) of Intermediate L-4, 8.64 g (22.27 mmol) of Intermediate L-10, 2.65 g (27.57 mmol) of sodium t-butoxide, 0.58 g (0.64 mmol) of Pd(dba)$_2$, 0.93 mL of tri t-butylphosphine (50% in toluene), and 85 ml of the toluene were put in a 500 mL flask and then, heated and stirred at 130° C. under a nitrogen flow. After 15 hours, a reaction was completed. The resultant was added to 500 mL of methanol, and a crystallized solid was filtered, dissolved in toluene, filtered with silica gel/Celite, and recrystallized with methanol after removing an appropriate amount of the organic solvent to obtain Intermediate A-5 (13.2 g, 80%). An elemental analysis result of the produced compound is as follows.

calcd. C57H38N4: C, 87.89; H, 4.92; N, 7.19; found: C, 87.82; H, 4.91; N, 7.22;

Example 3: Synthesis of Example A-7

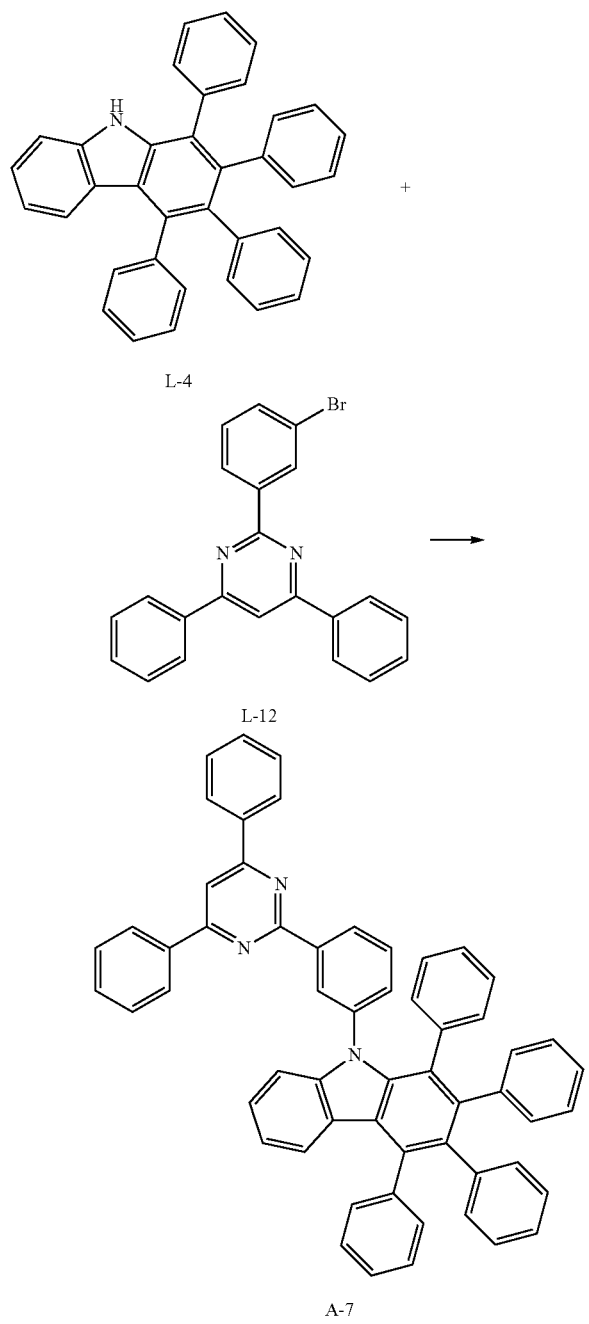

10 g (21.20 mmol) of Intermediate L-4, 8.62 g (22.27 mmol) of Intermediate L-12, 2.65 g (27.57 mmol) of sodium t-butoxide, 0.58 g (0.64 mmol) of Pd(dba)$_2$, and 0.93 mL of tri t-butylphosphine (50% in toluene), and 85 ml of the toluene were put in a 500 mL flask and then, heated and stirred under a nitrogen flow at 130° C. After 15 hours, a reaction was completed. The resultant was added to 500 mL of methanol, and a crystallized solid was filtered, dissolved in toluene, filtered again with silica gel/Celite, and recrystallized with methanol after removing an appropriate amount of the organic solvent to obtain Intermediate A-7 (11.8 g, 72%). An elemental analysis result of the produced compound is as follows.

calcd. C57H38N4: C, 89.55; H, 5.05; N, 5.40; found: C, 89.45; H, 5.11; N, 5.44;

Example 4: Synthesis of Compound A-12

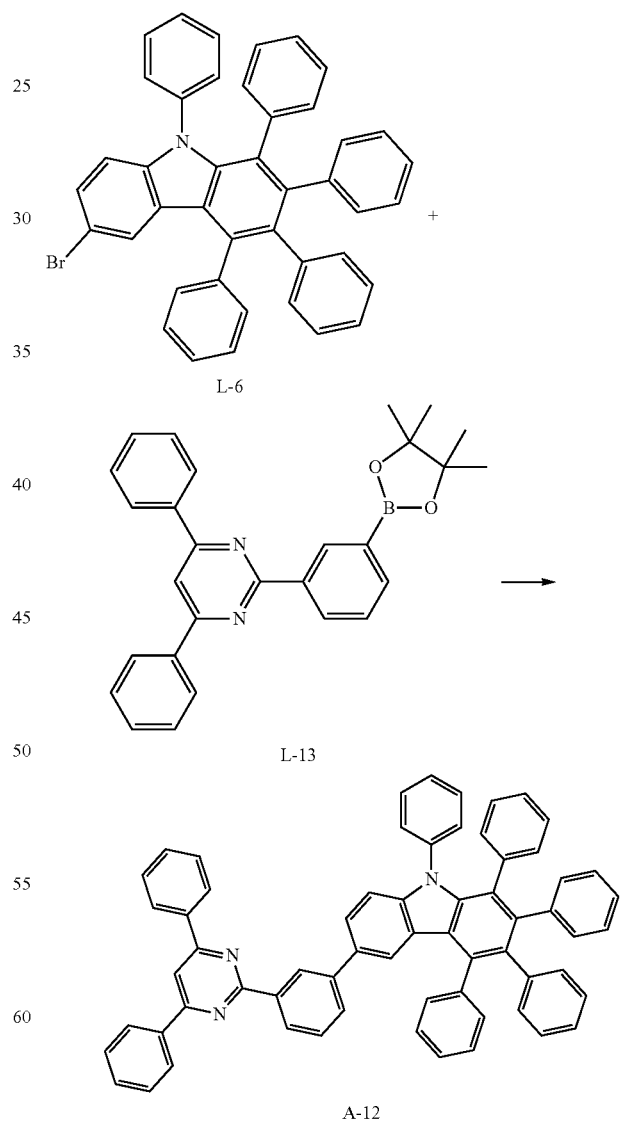

15.0 g (23.93 mmol) of Intermediate L-6, 11.13 g (25.62 mmol) of Intermediate L-13, 8.27 g (59.85 mmol) of potassium carbonate, 1.38 g (1.20 mmol) of Pd(PPh₃)₄ (tetrakis (triphenyl phosphine) palladium (0)), 100 mL of tetrahydrofuran, and 30 mL of water were put in a 250 mL flask and then, heated and refluxed under a nitrogen flow for 12 hours. The mixture was added to 500 mL of methanol, and a crystallized solid was dissolved in toluene, filtered with silica gel/Celite, and recrystallized with methanol after removing an appropriate amount of the organic solvent to obtain Compound A-12 (15.21 g, 74%). An elemental analysis result of the produced compound is as follows.

calcd. $C_{64}H_{43}N_3$: C, 90.01; H, 5.07; N, 4.92; found: C, 90.21; H, 5.11; N, 4.90;

Example 5: Synthesis of Compound A-13

<Reaction Scheme 14>

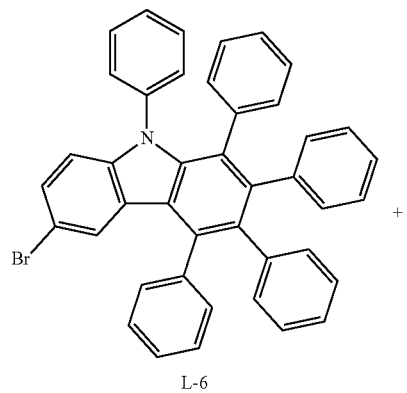

L-6

+

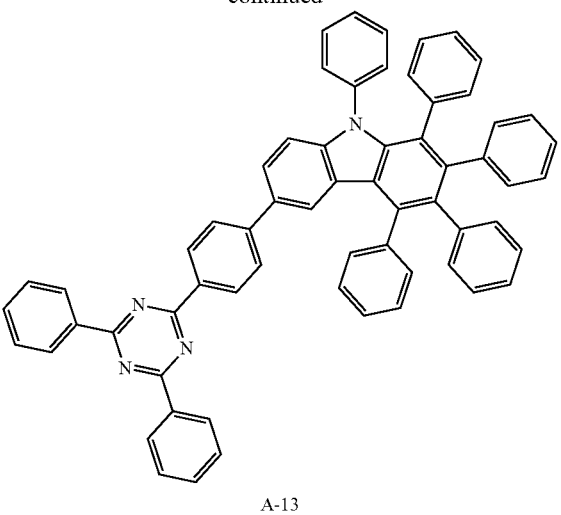

A-13

15.0 g (23.93 mmol) of Intermediate L-6, 11.15 g (25.62 mmol) of Intermediate L-9, 8.27 g (59.85 mmol) of potassium carbonate, and 1.38 g (1.20 mmol) of Pd(PPh₃)₄ (tetrakis(triphenyl phosphine) palladium (0)), 100 mL of tetrahydrofuran, and 30 mL of water put in a 250 mL flask and then, heated and refluxed under a nitrogen flow for 12 hours. The resultant was added to 500 mL of methanol, and a crystallized solid was filtered, dissolved in toluene, filtered again with silica gel/Celite, and recrystallized with methanol after removing an appropriate amount of the organic solvent to obtain Compound A-13 (15.10 g, 74%). An elemental analysis result of the produced compound is as follows.

calcd. $C_{63}H_{42}N_4$: C, 88.50; H, 4.95; N, 6.55; found: C, 88.40; H, 4.97; N, 6.58;

Example 6: Synthesis of Compound A-14

<Reaction Scheme 15>

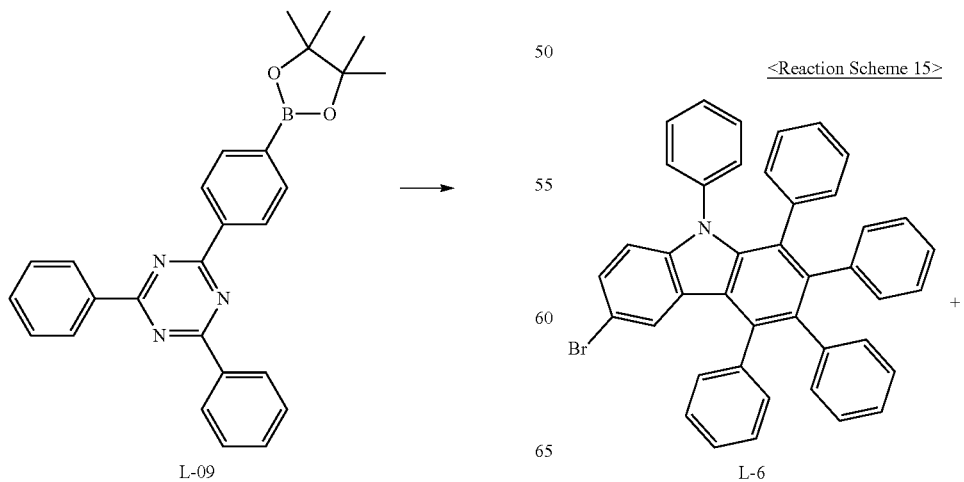

L-09      L-6

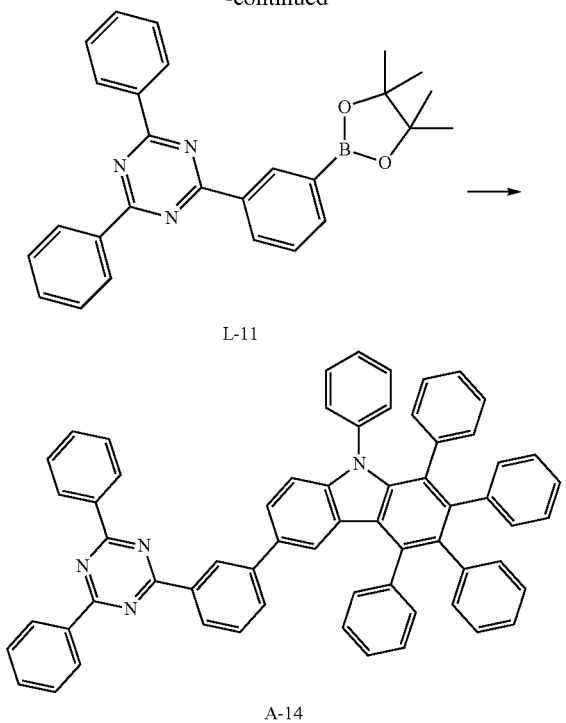

L-11

A-14

15.0 g (23.93 mmol) of Intermediate L-6, 11.15 g (25.62 mmol) of Intermediate L-11, 8.27 g (59.85 mmol) of potassium carbonate, and 1.38 g (1.20 mmol) of Pd(PPh$_3$)$_4$DeletedTexts(tetrakis(triphenyl phosphine)palladium (0)) were added to 100 mL of tetrahydrofuran and 30 mL of water in a 250 mL flask, and the mixture was heated and refluxed under a nitrogen flow for 12 hours. The resultant was added to 500 mL of methanol, and a crystallized solid was filtered, dissolved in toluene, filtered again with silica gel/Celite, and recrystallized with methanol after removing an appropriate amount of the organic solvent to obtain Compound A-14 (13.23 g, 65%). An elemental analysis result of the produced compound is as follows.

calcd. C$_{63}$H$_{42}$N$_4$: C, 88.50; H, 4.95; N, 6.55; found: C, 88.46; H, 4.90; N, 6.51;

Comparative Example 1: Synthesis of CBP

A compound represented by Chemical Formula a was synthesized according to the same method as a method disclosed in International Publication WO 2013-032035A (Example 18).

Chemical Formula a

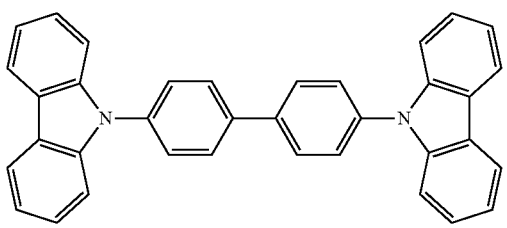

(Comparison of Simulation Characteristics of Compounds for Organic Optoelectronic Element)

An energy level of each material was calculated in a Gaussian 09 method by using Super Computer GAIA (IBM power 6), and the results are shown in Table 1.

TABLE 1

|  | Compound | HOMO (eV) | LUMO (eV) | T1 (eV) | S1 (eV) |
| --- | --- | --- | --- | --- | --- |
| Comparative Example 1 | CBP | −5.319 | −1.231 | 2.971 | 3.560 |
| Example 1 | A-4 | −5.316 | −1.917 | 2.757 | 2.944 |
| Example 2 | A-5 | −5.283 | −1.925 | 2.812 | 2.886 |
| Example 3 | A-7 | −5.198 | −1.746 | 2.941 | 3.087 |
| Example 4 | A-12 | −5.126 | −1.615 | 2.876 | 3.154 |
| Example 5 | A-13 | −5.219 | −1.745 | 2.837 | 3.104 |
| Example 6 | A-14 | −5.253 | −1.734 | 2.645 | 3.168 |

As shown in Table 1, when desired HOMO/LUMO energy levels are respectively in a range of −5.0 eV to −5.5 eV and in a range of −1.7 eV to −2.0 eV in a simulation, sufficient electron transport characteristics may be secured, but the Compound according to Comparative Example 1 satisfied the HOMO level but not the LUMO level and thus showed no balance between holes and electrons compared with the Compounds A-4, A-5, A-7, A-12, A-13, and A-14 according to the present invention.

(Manufacture of Organic Light Emitting Diode)

Device Comparative Example 1

Specifically, the organic light emitting diode was manufactured in a method of cutting an ITO glass substrate having sheet resistance of 15 Ω/cm$^2$ into a size of 50 mm×50 mm×0.7 mm, ultrasonic wave-cleaning it in acetone, isopropyl alcohol, and pure water respectively for 15 minutes, and UV ozone-cleaning it for 30 minutes to obtain an anode.

This ITO transparent electrode was 1000 Å thick and used as the anode, and the following HTM compound was vacuum-deposited to form a 1200 Å-thick hole injection layer (HIL) on the ITO substrate.

[HTM]

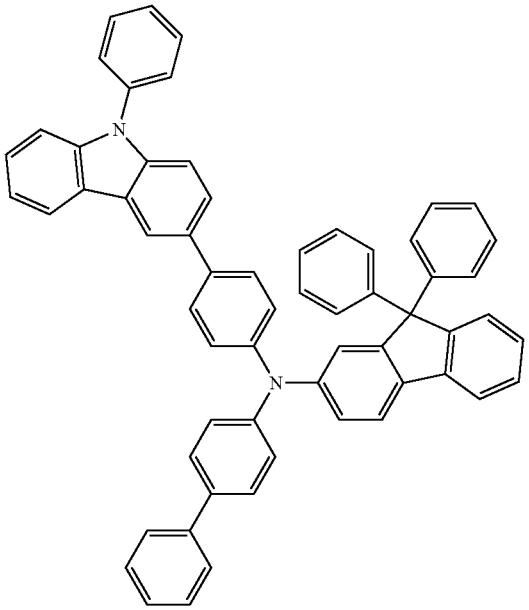

Then, a 300 Å thick light-emitting layer was formed by doping 4,4-N,N-dicarbazolebiphenyl (CBP) as a host with 7 wt % of the following PhGD compound as a phosphorescent green dopant and vacuum-depositing the doped CBP.

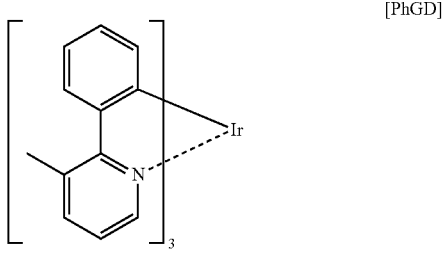

[PhGD]

On the light-emitting layer, an electron transport layer (ETL) was formed by sequentially depositing BAlq [bis(2-methyl-8-quinolinolato-N1,O8)-(1,1'-biphenyl-4-olato)aluminum] to be 50 Å thick and Alq3 [tris(8-hydroxyquinolinato) aluminum] to be 250 Å thick.

On the electron transport layer (ETL), LiF is vacuum-deposited to be 5 Å thick, and sequentially, Al is vacuum-deposited to be 1000 Å thick to form a cathode and thus, manufacture the organic light emitting diode.

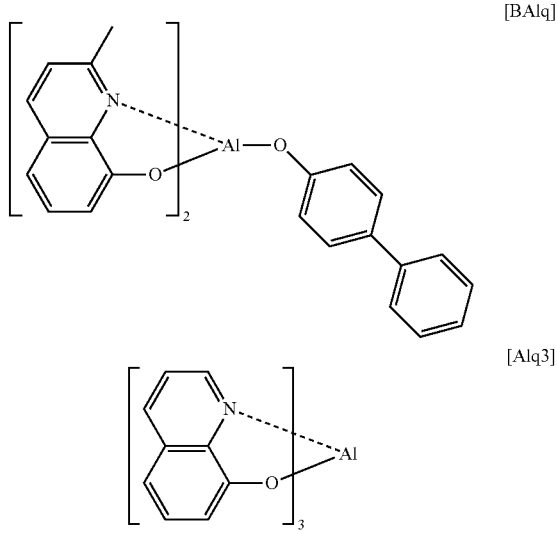

[BAlq]

[Alq3]

Device Example 1

An organic light emitting diode was manufactured according to the same method as Comparative Example 1 except for using the Compound A-4 of Example 1 instead of the CBP to form the light-emitting layer.

Device Example 2

An organic light emitting diode was manufactured according to the same method as Comparative Example 1 except for using the Compound A-5 of Example 2 instead of the CBP to form the light-emitting layer.

Device Example 3

An organic light emitting diode was manufactured according to the same method as Comparative Example 1 except for using the Compound A-7 of Example 3 instead of the CBP to form the light-emitting layer.

Device Example 4

An organic light emitting diode was manufactured according to the same method as Comparative Example 1 except for using the Compound A-12 of Example 4 instead of the CBP to form the light-emitting layer.

Device Example 5

An organic light emitting diode was manufactured according to the same method as Comparative Example 1 except for using the Compound A-13 of Example 5 instead of the CBP to form the light-emitting layer.

Device Example 6

An organic light emitting diode was manufactured according to the same method as Comparative Example 1 except for using the Compound A-14 of Example 6 instead of the CBP to form the light-emitting layer.

(Performance Measurement of Organic Light Emitting Diode)

A current density change, a luminance change, and luminous efficiency of each organic light emitting diode according to Examples 1 to 6 and Comparative Example 1 were measured.

Specific measurement methods are as follows, and the results are shown in Table 2.

(1) Measurement of Current Density Change Depending on Voltage Change

The obtained organic light emitting diodes were measured regarding a current value flowing in a unit device by using a current-voltage meter (Keithley 2400), while a voltage was increased from 0 V to 10 V, and the measured current value was divided by an area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) was calculated by using the luminance, current density, and voltages (V) from the items (1) and (2).

(4) Measurement of Life-Span

A life span was obtained by measuring a time when current efficiency (cd/A) was decreased down to 90%, while luminance (cd/m$^2$) was maintained to be 5000 cd/m$^2$.

TABLE 2

| No. | Light-emitting layer | Color (EL color) | Driving voltage (V) | Efficiency (cd/A) |
|---|---|---|---|---|
| Example 1 | A-4 | green | 4.05 | 59.2 |
| Example 2 | A-5 | green | 4.08 | 57.3 |
| Example 3 | A-7 | green | 4.36 | 52.3 |
| Example 4 | A-12 | green | 4.42 | 51.4 |
| Example 5 | A-13 | green | 4.13 | 58.6 |
| Example 6 | A-14 | green | 4.16 | 56.9 |
| Comparative Example 1 | CBP | green | 6.70 | 34.8 |

As shown in Table 2, Examples showed overall early 4 of a driving voltage and were lower than Comparative Example 1 and in addition, showed about 1.5 times increased luminous efficiency compared with Comparative Example 1. In other words, as the driving voltage and luminous efficiency were increased, improved characteristics in terms of power efficiency were obtained.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic element represented by Chemical Formula 1:

[Chemical Formula 1]

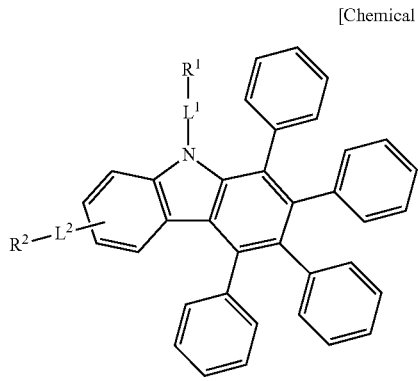

wherein, in Chemical Formula 1,

R$^1$ and R$^2$ are independently hydrogen, a substituted or unsubstituted C6 to C30 aryl group, a substituted or unsubstituted C2 to C30 heterocyclic group, a substituted or unsubstituted C6 to C30 arylamine group, or a combination thereof, at least one of R$^1$ and R$^2$ is a substituted or unsubstituted group of Group I, L$^1$ and L$^2$ are independently a single bond, a substituted or unsubstituted C6 to C30 arylene group, a substituted or unsubstituted C2 to C30 heteroarylene group, or a combination thereof,

[Group I]

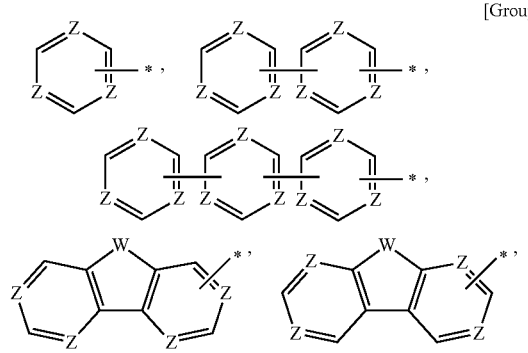

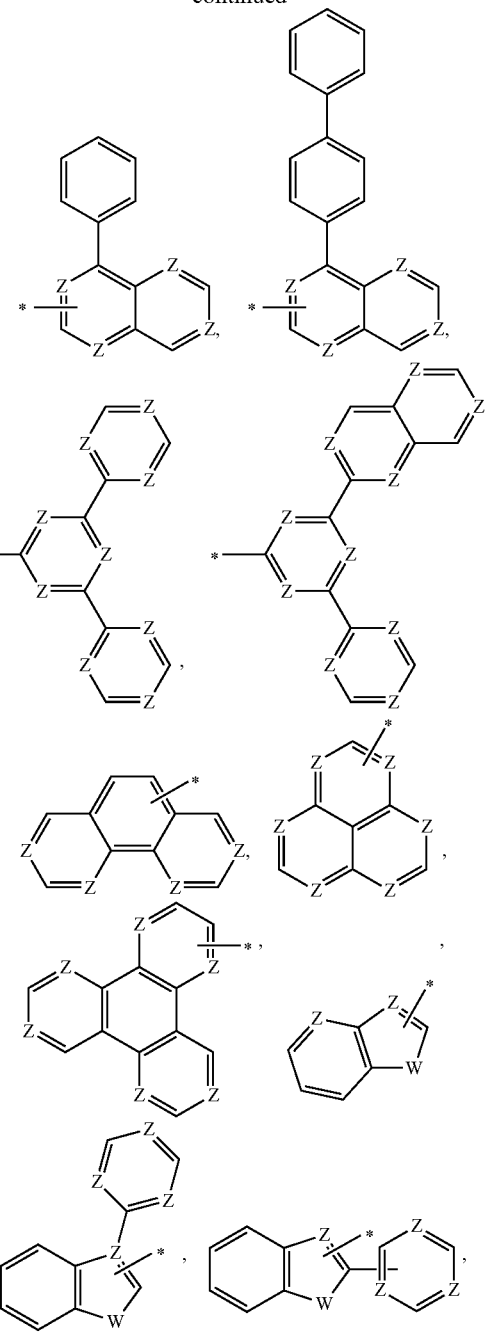

wherein, in Group I,

Z is independently N or CR$^a$, provided that at least one of Z is N, and

W is O, S or CR$^c$R$^d$, wherein R$^a$, R$^c$ and R$^d$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and wherein "substituted" refers to replacement of at least one hydrogen by a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a C1 to C10 trifluoroalkyl group, or a cyano group.

2. The compound for an organic optoelectronic element of claim 1, wherein Chemical Formula 1 is represented by one of Chemical Formula 1-a, 1-b, and 1-c:

[Chemical Formula 1-a]

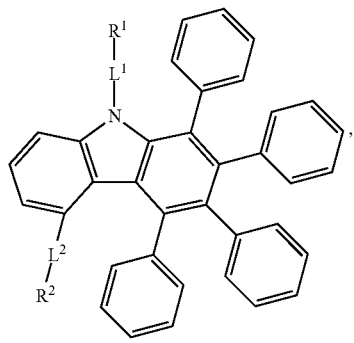

[Chemical Formula 1-b]

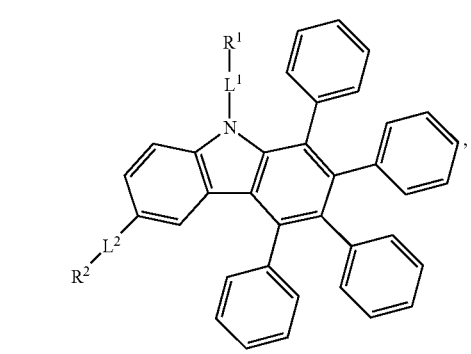

[Chemical Formula 1-c]

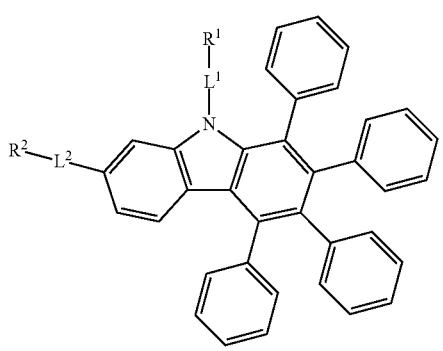

wherein, in Chemical Formula 1-a, 1-b, and 1-c, $R^1$ and $R^2$ are independently hydrogen, a substituted or unsubstituted C6 to C30 aryl group, a substituted or unsubstituted C2 to C30 heterocyclic group, a substituted or unsubstituted C6 to C30 arylamine group, or a combination thereof, at least one of $R^1$ and $R^2$ is a substituted or unsubstituted group of Group I, $L^1$ and $L^2$ are independently a single bond, a substituted or unsubstituted C6 to C30 arylene group, a substituted or unsubstituted C2 to C30 heteroarylene group, or a combination thereof,

[Group I]

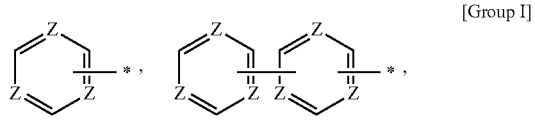

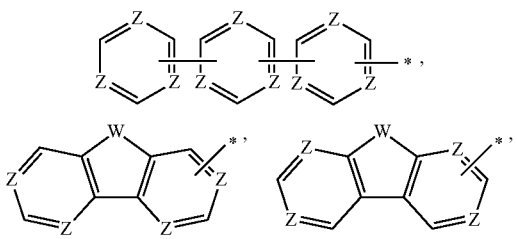

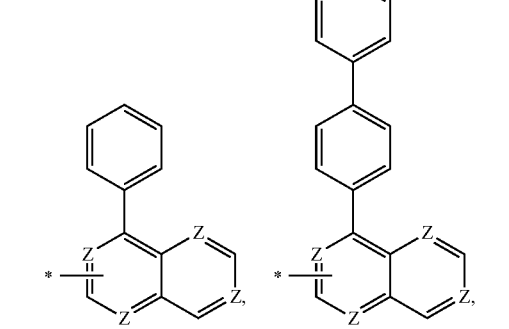

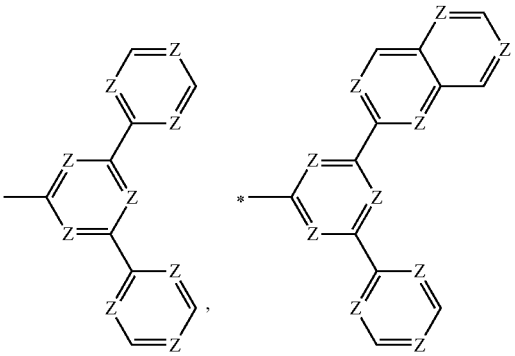

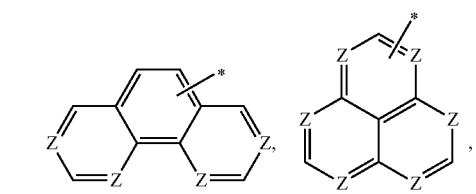

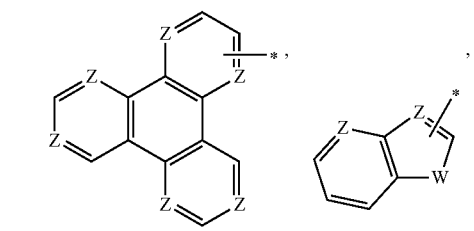

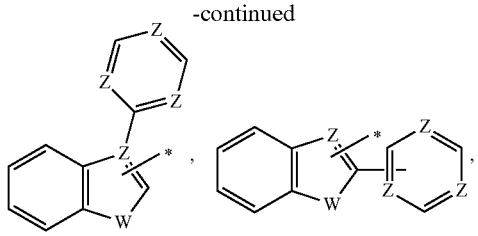

wherein, in Group I,
Z is independently N or CR$^a$, provided that at least one of Z is N, and
W is O, S or CR$^c$R$^d$,
wherein R$^a$, R$^c$ and R$^d$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, or a substituted or unsubstituted C2 to C30 heteroaryl group, and
wherein "substituted" refers to replacement of at least one hydrogen by a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a C1 to C10 trifluoroalkyl group, or a cyano group.

3. The compound for an organic optoelectronic element of claim 1, wherein R$^1$ and R$^2$ are independently hydrogen, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted azaphenanthrenyl group, a substituted or unsubstituted phenanthrolinyl group, a substituted or unsubstituted phenazinyl group, or a combination thereof.

4. The compound for an organic optoelectronic element of claim 1, wherein the substituted or unsubstituted nitrogen-containing C2 to C30 heterocyclic group except a carbazolyl group is a substituted or unsubstituted imidazolyl group, a substituted or unsubstituted triazolyl group, a substituted or unsubstituted tetrazolyl group, a substituted or unsubstituted oxadiazolyl group; a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

5. The compound for an organic optoelectronic element of claim 1, wherein the substituted or unsubstituted group of Group I is a group of Group I-1:

[Group I-1]

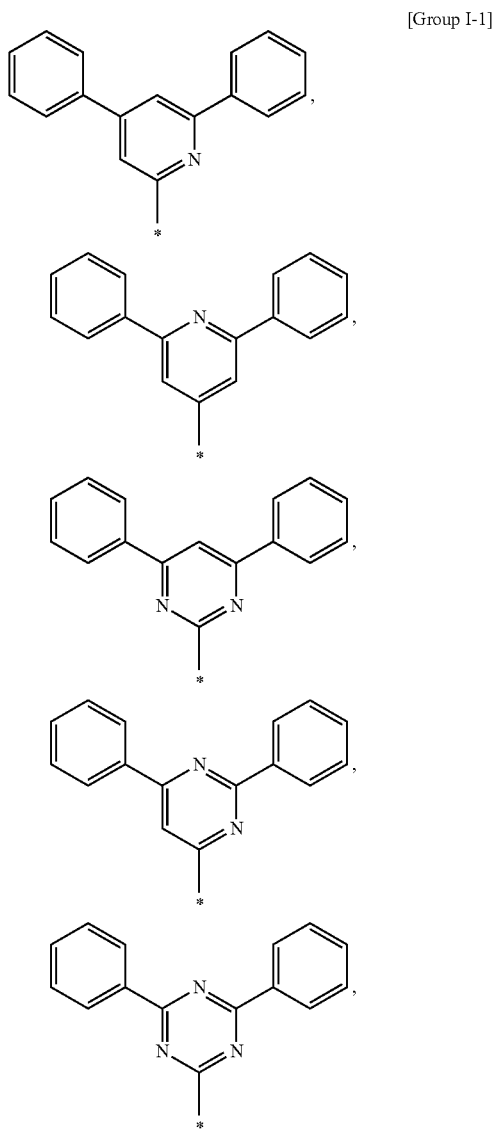

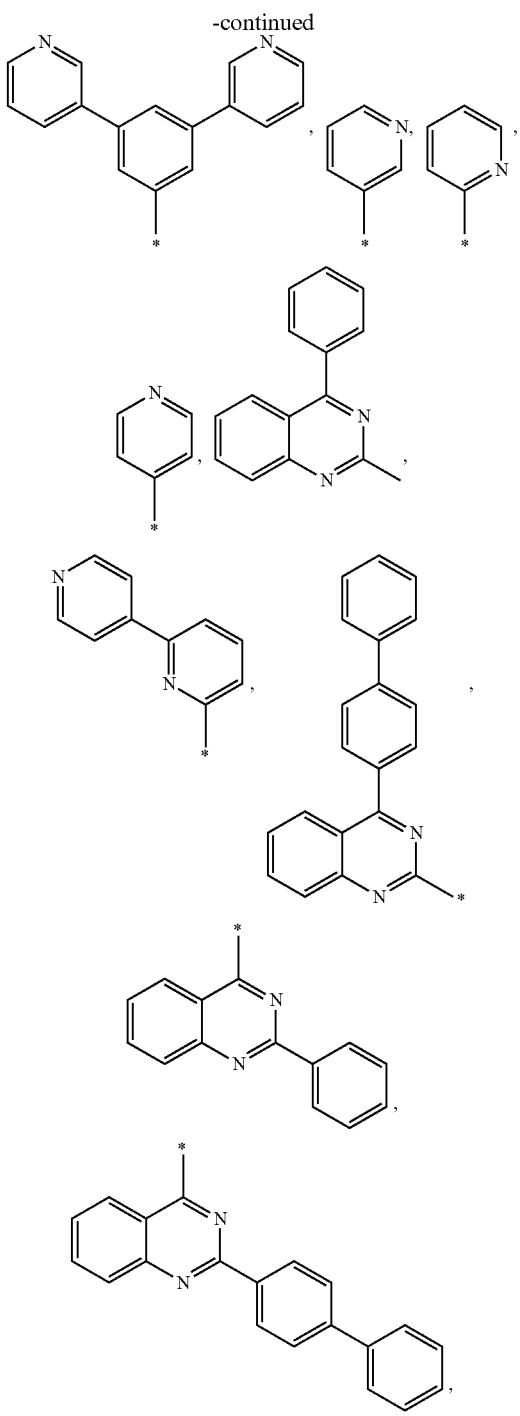

wherein, in Group I-1, is a linking point.

6. The compound for an organic optoelectronic element of claim 1, wherein the $L^1$ and $L^2$ are independently a single bond, a substituted or unsubstituted phenylene group, a substituted or unsubstituted biphenylene group, a substituted or unsubstituted naphthyl group, a substituted or unsubstituted pyridinyl group, a substituted or unsubstituted pyridmidyl group, a substituted or unsubstituted triazinyl group, a substituted or unsubstituted phenylquinazoline group, or a combination thereof.

7. The compound for an organic optoelectronic element of claim 1, wherein the $L^1$ and $L^2$ are independently a single bond or one selected from substituted or unsubstituted groups of Group II:

[Group II]

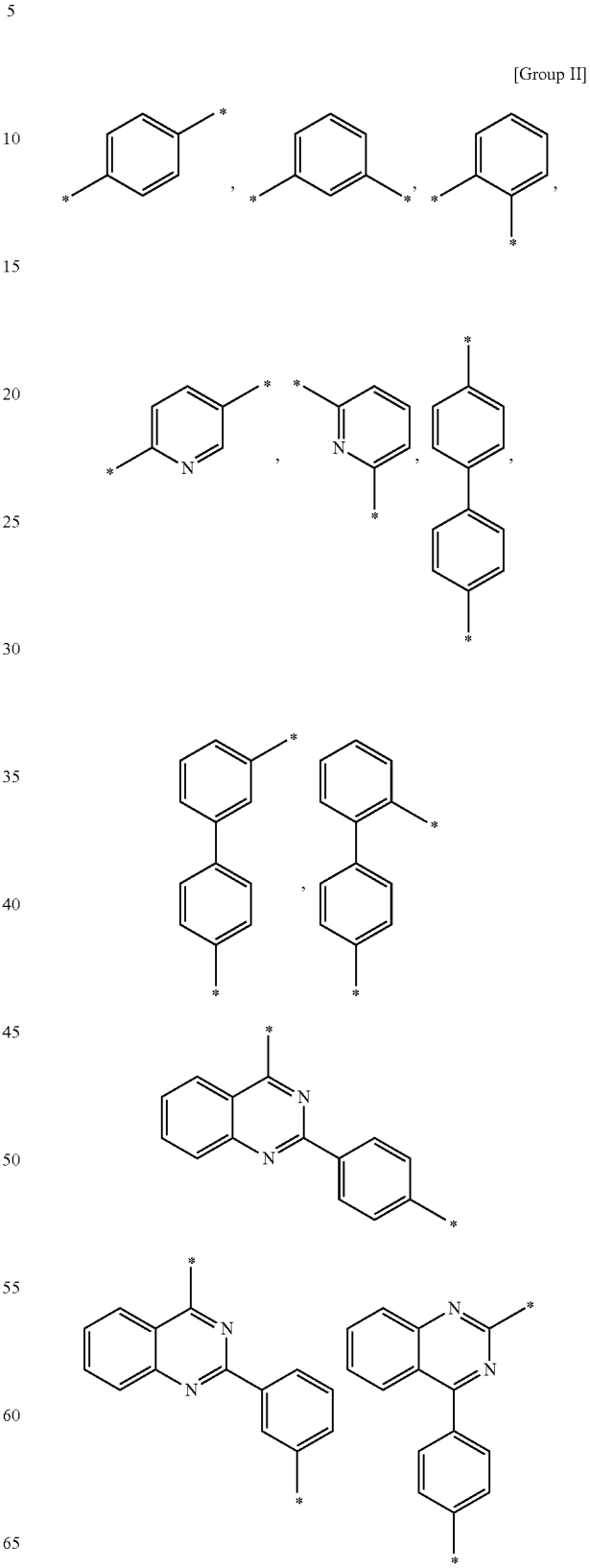

-continued

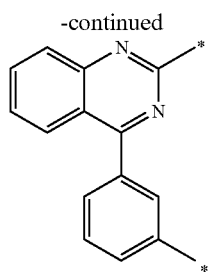

wherein, in Group II,
is a linking point,
wherein "substituted" refers to replacement of at least one hydrogen by a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a C1 to C10 trifluoroalkyl group, or a cyano group.

8. The compound for an organic optoelectronic element of claim 1, wherein one of $R^1$ and $R^2$ is selected from a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, and a substituted or unsubstituted phenazinyl group, as a substituted or unsubstituted nitrogen-containing C2 to C30 heterocyclic group except a carbazolyl group;
the other of $R^1$ and $R^2$ is selected from hydrogen, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted dibenzothiophenyl group, a substituted or unsubstituted dibenzofuranyl group, a substituted or unsubstituted carbazole group; and
$L^1$ and $L^2$ are independently a single bond or a substituted or unsubstituted C6 to C30 arylene group.

9. The compound for an organic optoelectronic element of claim 1, wherein the compound represented by Chemical Formula 1 is selected from Chemical Formula A-1 to Chemical Formula A-45:

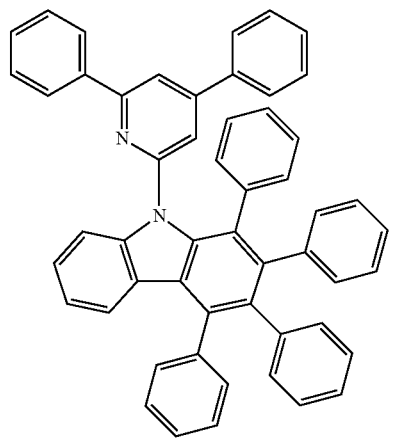

[A-1]

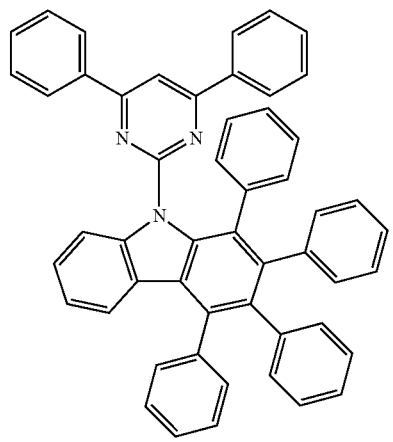

[A-2]

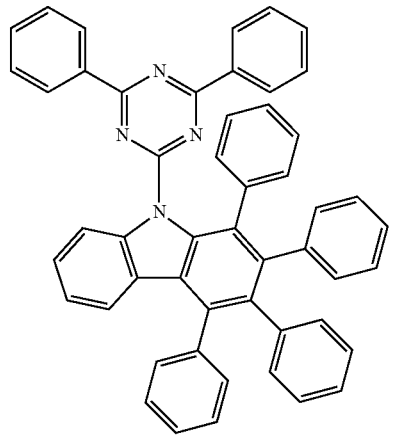

[A-3]

[A-4]
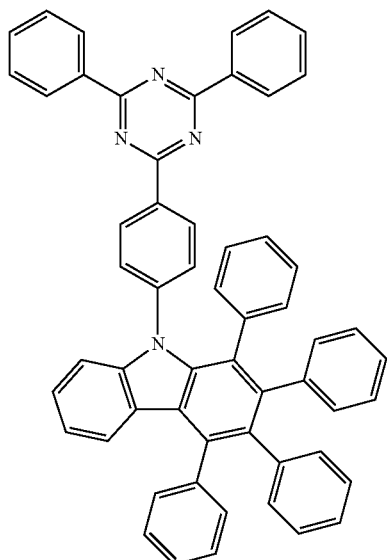
[A-5]
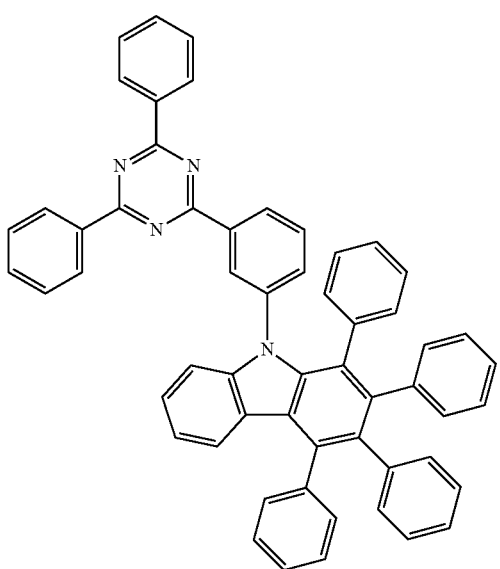
[A-6]
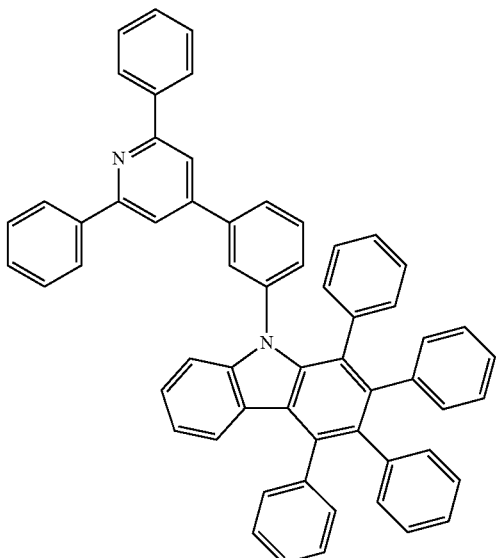
[A-7]
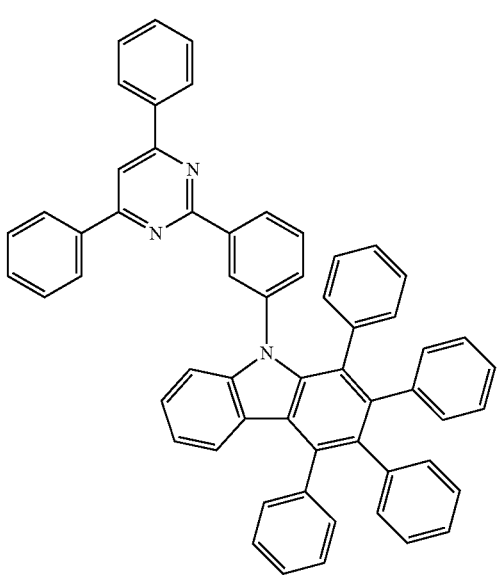

[A-8]
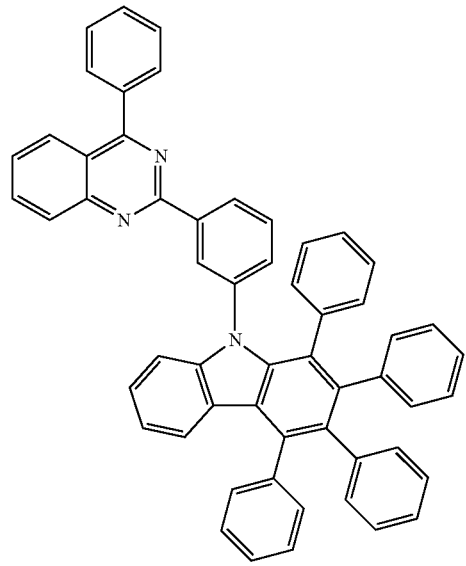
[A-10]
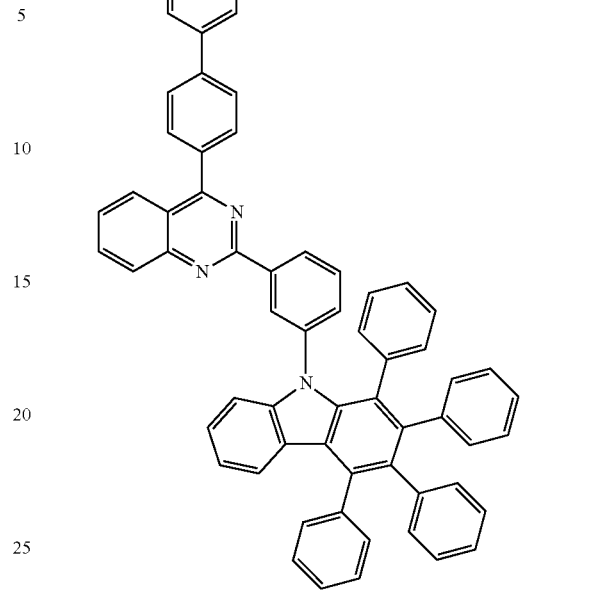
[A-11]
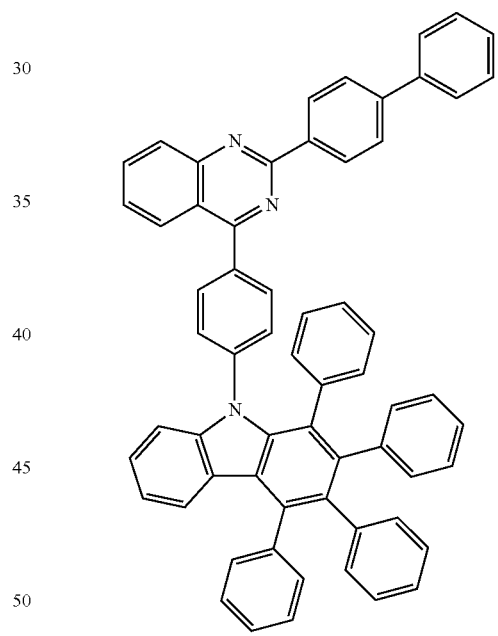
[A-9]
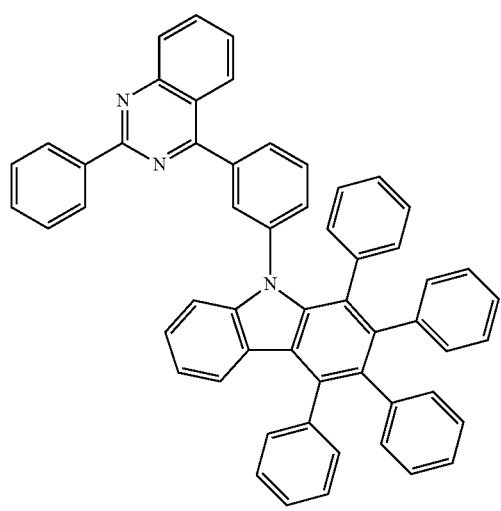
[A-12]
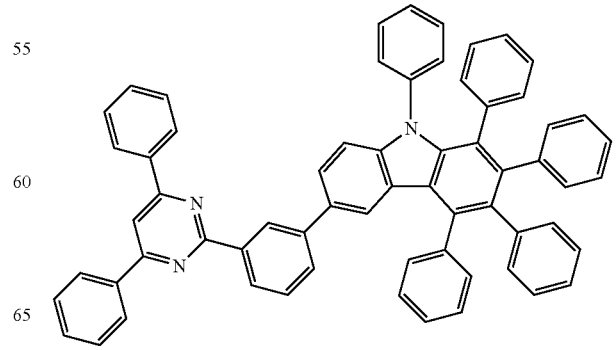

[A-13]
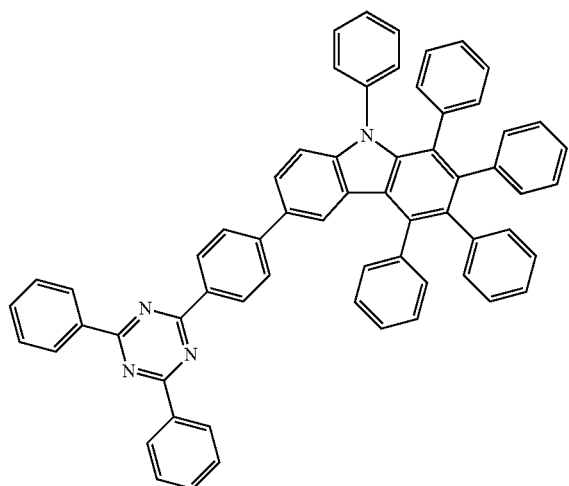
[A-14]
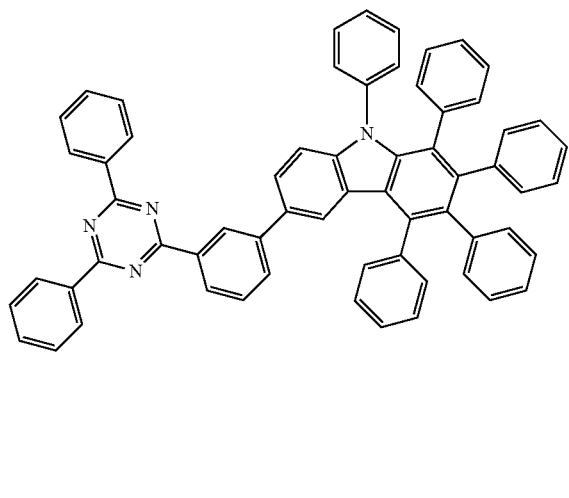
[A-15]
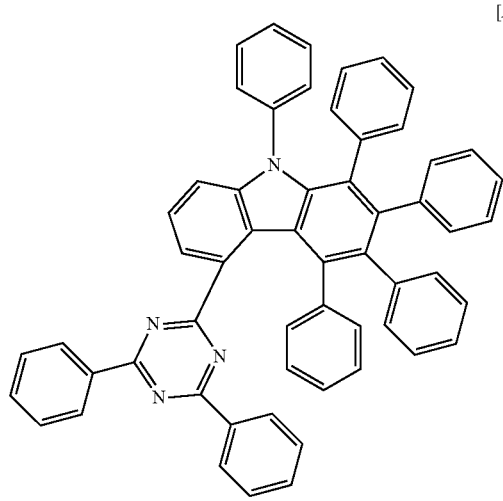
[A-16]
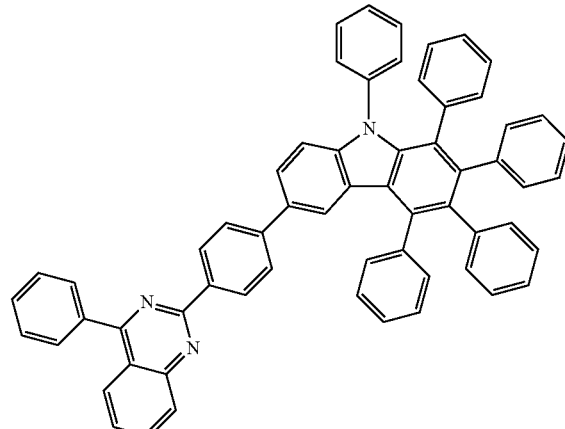
[A-17]
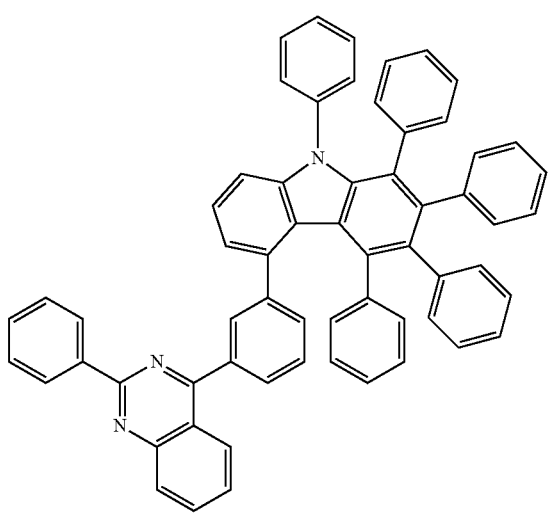
[A-18]
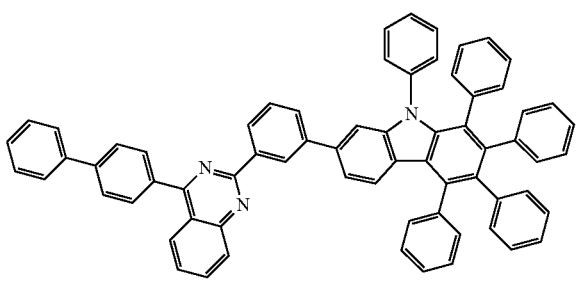

[A-19]
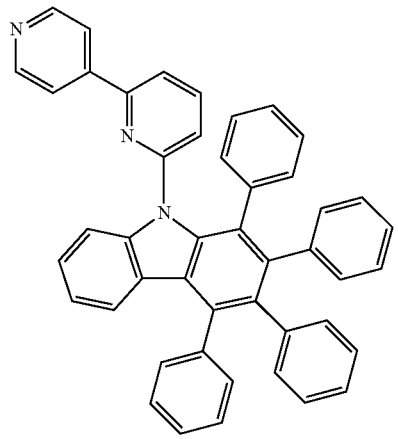
[A-20]
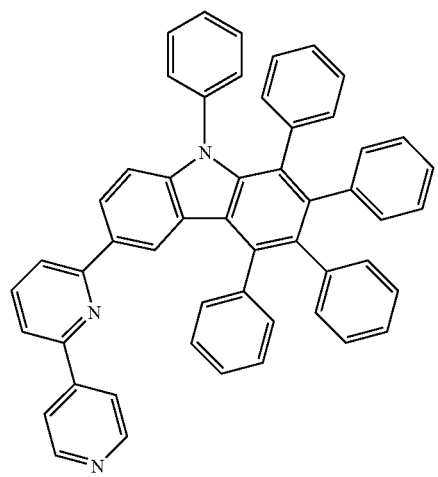
[A-21]
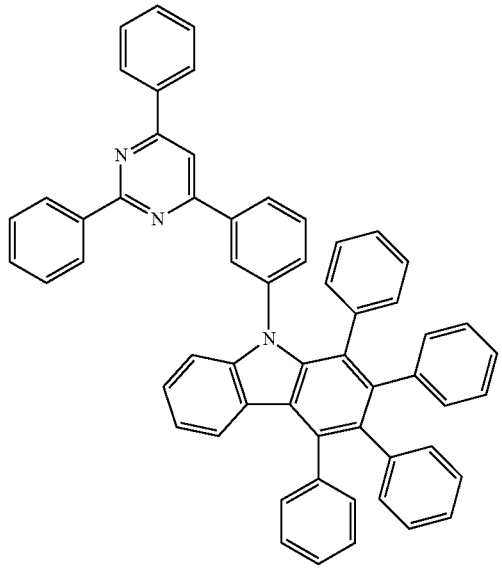
[A-22]
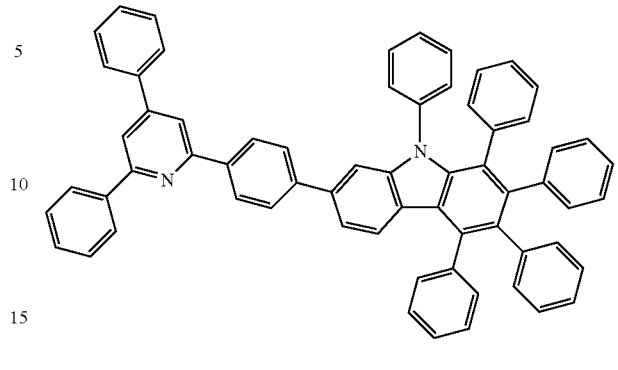
[A-23]
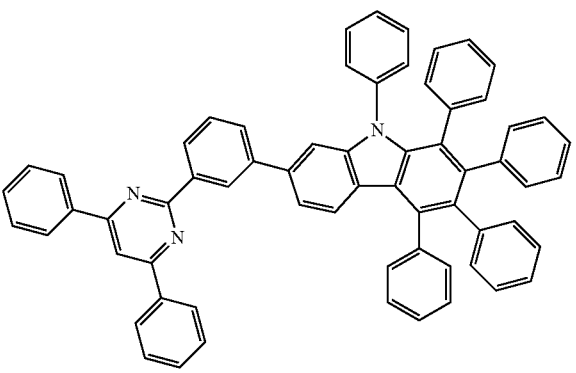
[A-24]
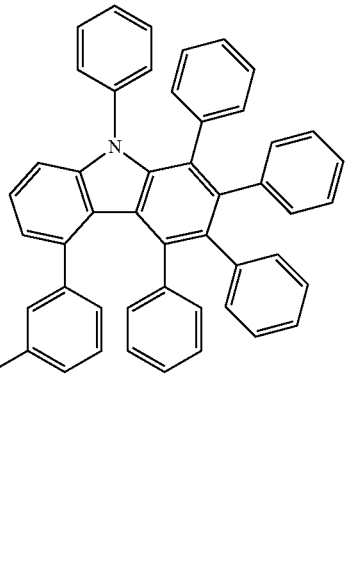

[A-25]
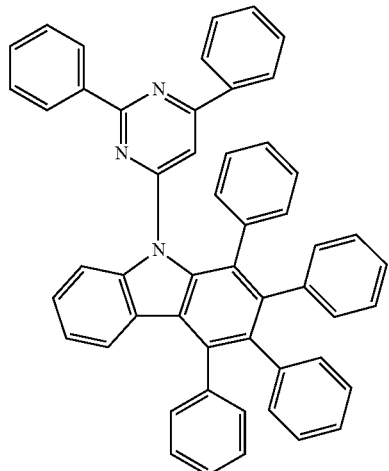
[A-28]
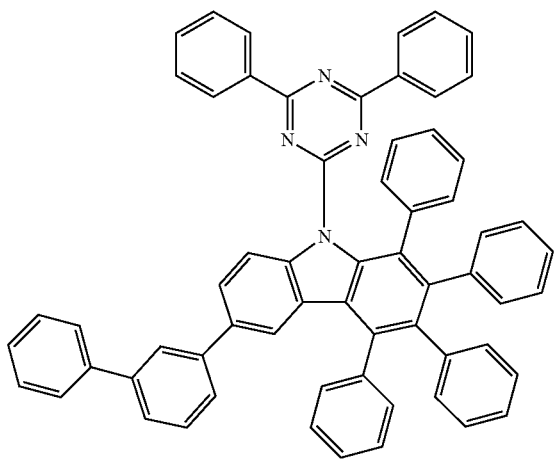
[A-26]
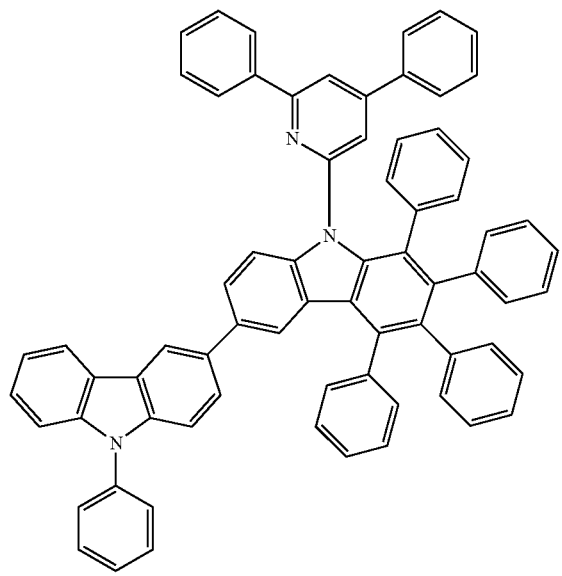
[A-27]
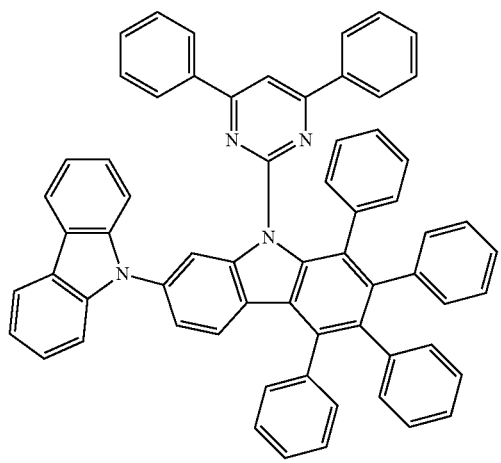
[A-29]
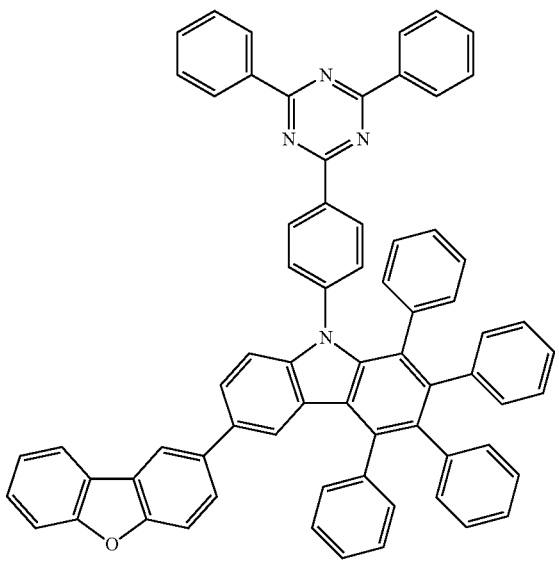

-continued
[A-30]
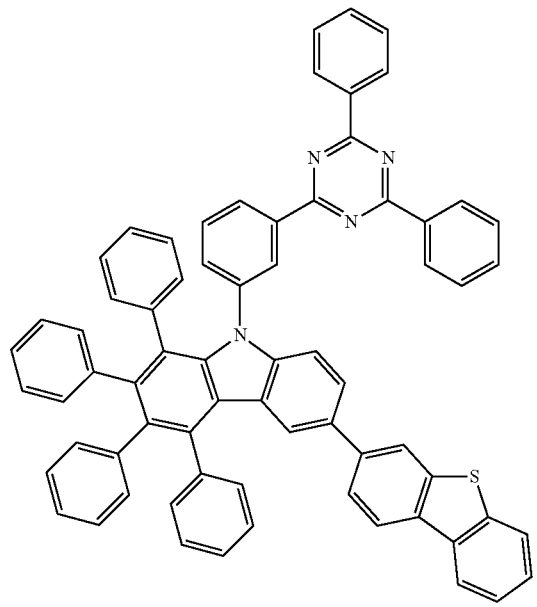
[A-31]
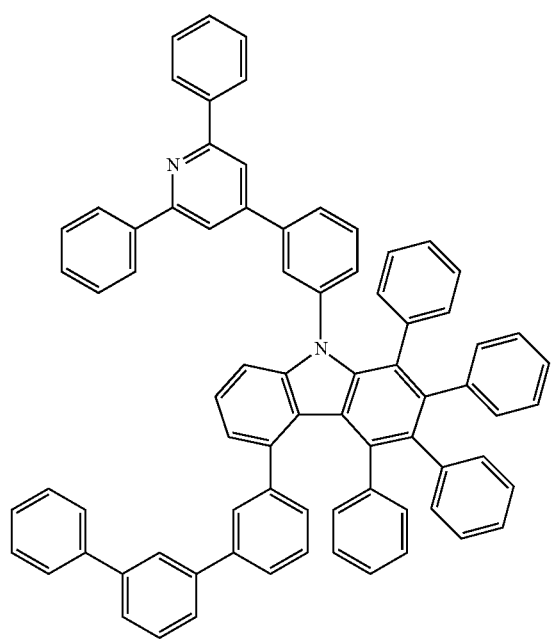
[A-32]
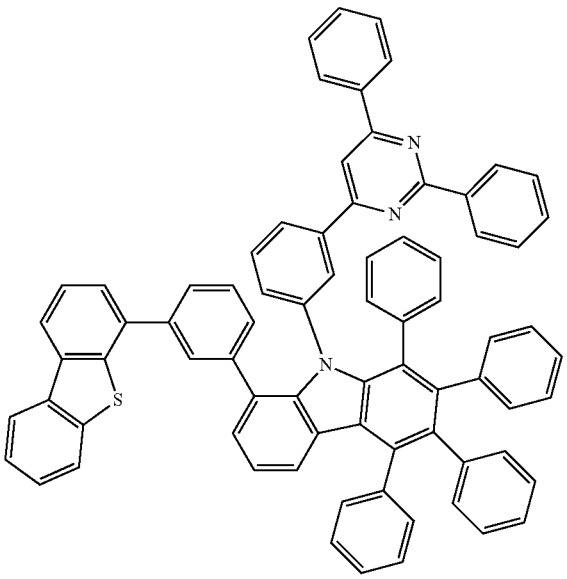
[A-33]
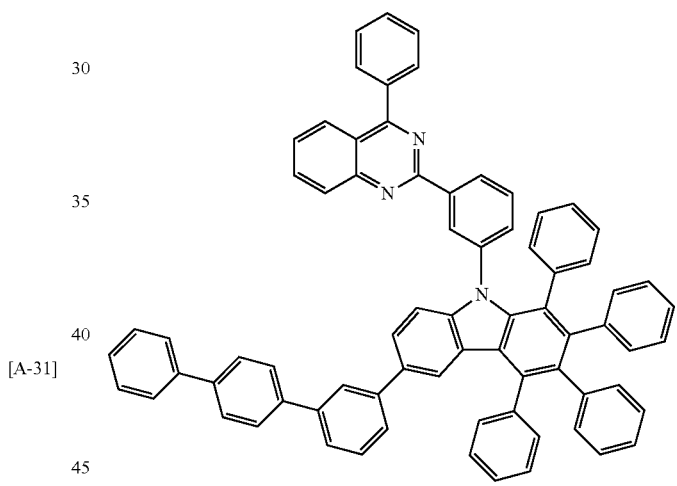
[A-34]
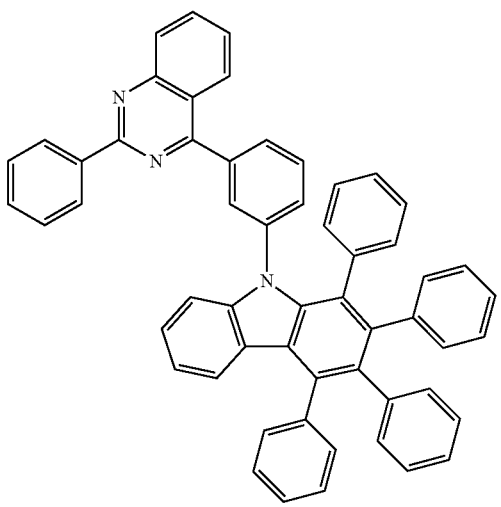

[A-35]
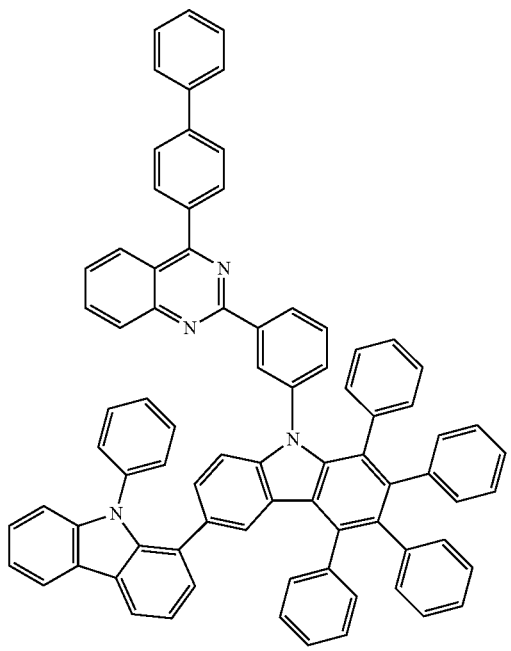
[A-37]
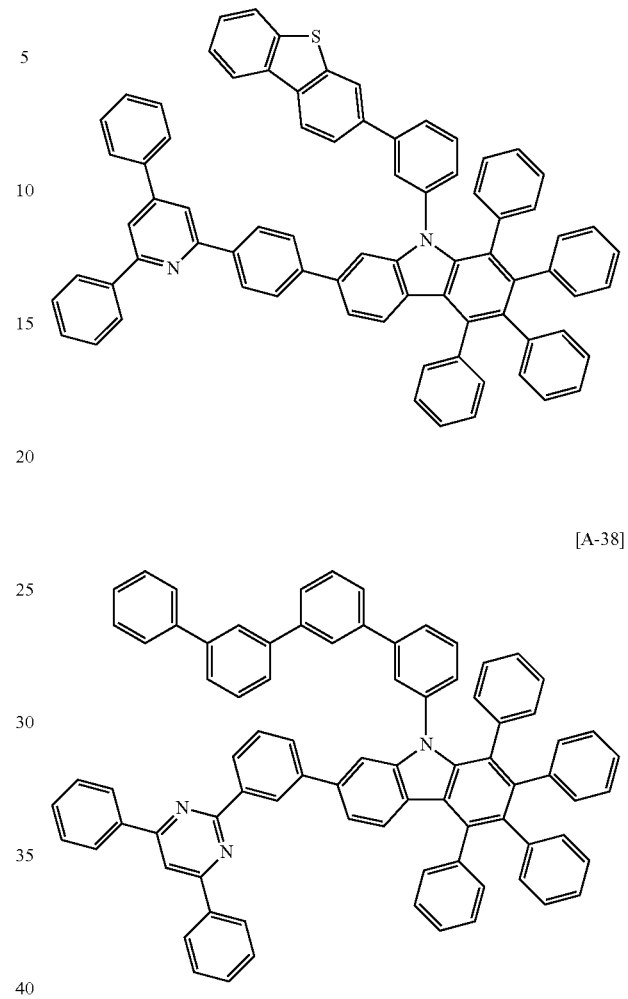
[A-38]
[A-36]
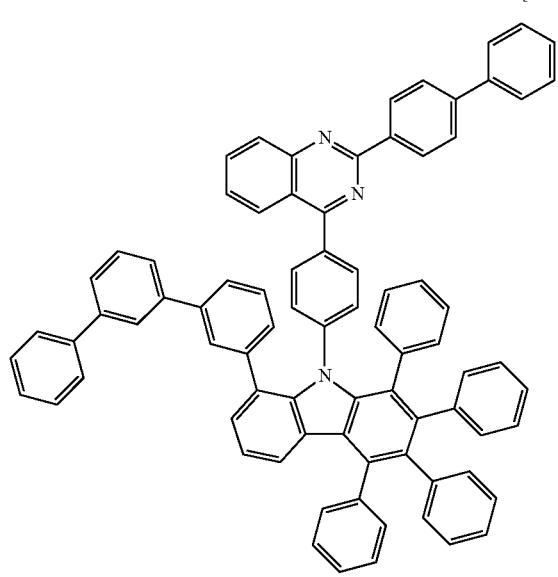
[A-39]
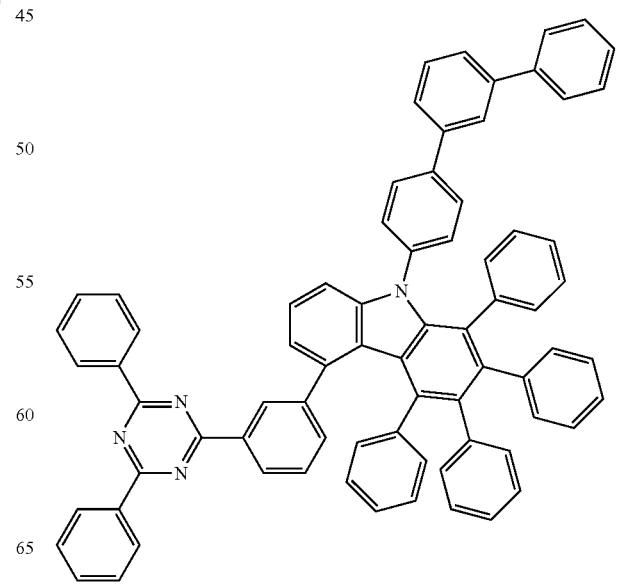

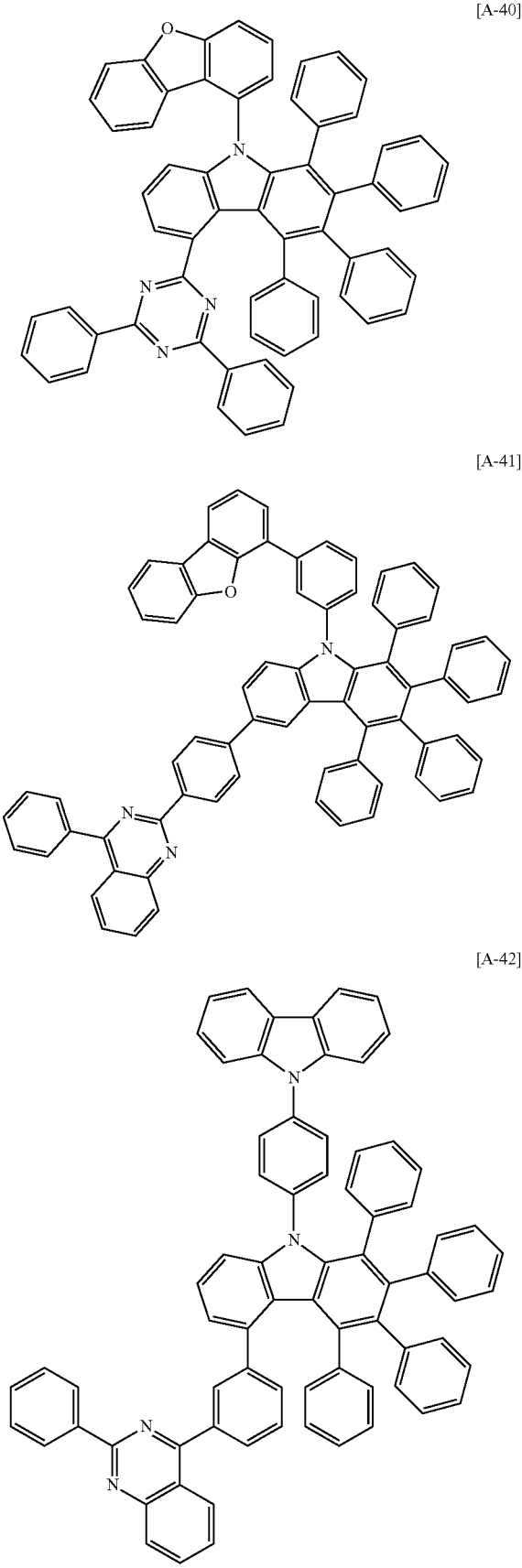
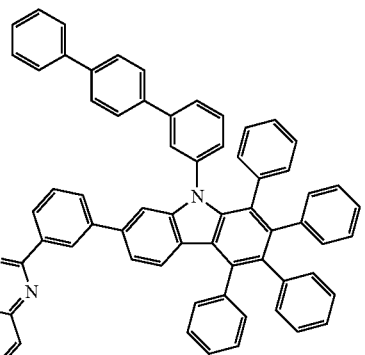
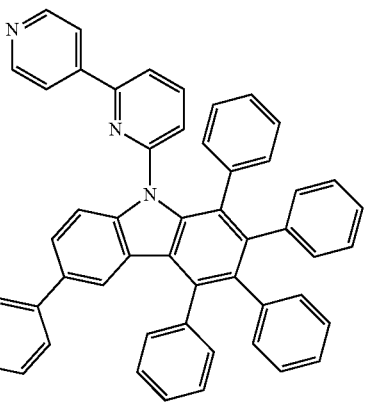

10. An organic optoelectronic element, comprising:
   an anode and a cathode facing each other, and
   at least one organic layer disposed between the anode and the cathode, the organic layer including the compound for an organic optoelectronic element of claim 1.

11. The organic optoelectronic element of claim 10, wherein the organic layer includes a light-emitting layer, and
   the light-emitting layer includes the compound for an organic optoelectronic element.

12. The organic optoelectronic element of claim 11, wherein the compound for an organic optoelectronic element is included as a host of the light-emitting layer.

13. The organic optoelectronic element of claim 10, wherein the organic layer includes at least one auxiliary layer selected from a hole injection layer, a hole transport layer, an auxiliary hole transport layer, an auxiliary electron transport layer, an electron transport layer, and an electron injection layer, and the auxiliary layer includes the compound for an organic optoelectronic element.

14. A display device comprising the organic optoelectronic element of claim 10.

* * * * *